United States Patent
Chen et al.

(10) Patent No.: US 9,744,165 B2
(45) Date of Patent: Aug. 29, 2017

(54) METHOD FOR TREATING HYPERTENSION

(71) Applicant: TSH Biopharm Corporation Ltd., Taipei (TW)

(72) Inventors: Jaw-Wen Chen, Taipei (TW); Hsi-Chieh Wang, Taipei (TW); Shin-Yi Juang, Taipei (TW)

(73) Assignee: TSH Biopharm Corporation Ltd., Taipei (TW)

( * ) Notice: Subject to any disclaimer, the term of this patent is extended or adjusted under 35 U.S.C. 154(b) by 0 days.

(21) Appl. No.: 15/141,381

(22) Filed: Apr. 28, 2016

(65) Prior Publication Data

US 2016/0235741 A1 Aug. 18, 2016

Related U.S. Application Data

(62) Division of application No. 13/695,628, filed as application No. PCT/CN2011/073560 on Apr. 29, 2011, now abandoned.

(60) Provisional application No. 61/330,540, filed on May 3, 2010.

(51) Int. Cl.
| | | |
|---|---|---|
| A61K 31/485 | (2006.01) | |
| A61K 31/44 | (2006.01) | |
| A61K 31/4422 | (2006.01) | |
| A61K 31/4709 | (2006.01) | |

(52) U.S. Cl.
CPC .......... *A61K 31/485* (2013.01); *A61K 31/44* (2013.01); *A61K 31/4422* (2013.01); *A61K 31/4709* (2013.01)

(58) Field of Classification Search
CPC .. A61K 31/4422; A61K 31/485; A61K 31/44; A61K 31/4709
See application file for complete search history.

(56) References Cited

U.S. PATENT DOCUMENTS

| 5,350,756 A | 9/1994 | Smith |
| 5,560,913 A | 10/1996 | Kupper |
| 2005/0107415 A1 | 5/2005 | Wu et al. |
| 2006/0188450 A1 | 8/2006 | Clarot |
| 2008/0039484 A1 | 2/2008 | Wu et al. |

FOREIGN PATENT DOCUMENTS

| CN | 101023947 A | 8/2007 |
| EP | 1505068 A1 | 2/2005 |
| JP | 04368338 A | 12/1992 |
| WO | WO 92/03137 | 3/1992 |
| WO | 03097608 A2 | 11/2003 |
| WO | 2006033965 A2 | 3/2006 |
| WO | WO 2007097765 A1 | 8/2007 |
| WO | 2009070744 A1 | 6/2009 |

OTHER PUBLICATIONS

Alvarez et al, "Role of NADPH oxidase and iNOS in vasoconstrictor responses of vessels from hypertensive and normotensive rats," British Journal of Pharmacology, vol. 153, pp. 926-935 (2008).

Britton et al, "Dextromethorphan protects against cerebral injury following transient, but not permanent, focal ischemia in rats," Life Sciences, vol. 60, No. 20, pp. 1729-1740 (1997).

Brown et al, "Mobidity and mortality in patients randomised to double-blind treatment with a long-acting calcium-channel blocker or diuretic in the International Nifedipine GITS study: Intervention as a Goal in Hypertension Treatment (INSIGHT)," Lancet, vol. 356, pp. 366-372 (Jul. 29, 2000).

Chobanian et al, "Seventh report of the joint national committee on prevention, detection, evaluation, and treatment of high blood pressure," Hypertension, vol. 42, pp. 1206-1252 (2003).

Dahlof et al, "Prevention of cardiovascular events with an antihypertensive regiment of amlodipine adding perindopril as required versus atenolol adding bendroftumethiasize as required, in the Anglo-Scandinavian Cardiac Outcomes Trial—Blood Pressure Lowering Arm (ASCOT-BPLA): a multicentre randomised controlled trial," Lancet, vol. 366, pp. 895-906 (Sep. 10, 2005).

Ezzati et al, "Selected major risk factors and global and regional burden of disease," Lancet, vol. 360, pp. 1347-1360 (Nov. 2, 2002).

Feng et al, Journal of Clinical Anesthesiology, vol. 22, No. 5, pp. 399-401 (May 2006).

Fogari et al. Effects of Amlodipine, Nifedipine GITS, and Indomethacin on Angiotensin-Converting Enzyme Inhibitor-Induced Cough: A Randomized, Placebo-Controlled, Double-Masked, Crossover Study. Curr. Ther. Res. 60(3), pp. 121-128 (1999).

George et al, "Dextromethorphan reduces neocortical ischemic neuronal damage in vivo," Brain Research, vol. 440, pp. 375-379 (1988).

Hansson et al, "Effects of intensive blood-pressure lowering and low-dose aspirin in patients with hypertension: principal results of the Hypertension Optimal Treatment (HOT) randomised trial," Lancet, vol. 351, pp. 1755-1762 (Jun. 13, 1998).

Int'l Search Report dated Aug. 18, 2011 in International Application No. PCT/CN2011/073560.

Julius et al, "Outcomes in hypertensive patients at high cardiovascular risk treated with regiments based on valsartan or amlodipine: the VALUE randomised trial," Lancet, vol. 363, pp. 2022-2031 (Jun. 19, 2004).

Kamei et al. Antitussive effects of Ca2+ channel antagonists. Eur. J. Pharm. 212, pp. 61-66 (1992).

Kearney et al, "Global burden of hypertension: analysis of worldwide data," Lancet, vol. 365, pp. 217-223 (Jan. 15, 2005).

Liu et al, "Comparison of active treatment and placebo in older Chinese patients with isolated systolic hypertension," Journal of Hypertension, vol. 16, pp. 1823-1829 (1998).

(Continued)

*Primary Examiner* — Barbara P Badio
*Assistant Examiner* — Sara E Townsley
(74) *Attorney, Agent, or Firm* — Perkins Coie LLP; Viola T. Kung

(57) ABSTRACT

Dextromethorphan is used to lower blood pressure in a subject suffering from hypertension, alone or in combination with another anti-hypertensive agent. In particular, dextromethorphan acts synergistically with a calcium channel blocker, such as amlodipine, to result in a major improvement in the treatment of hypertension, with no or little adverse effects.

5 Claims, 19 Drawing Sheets

(56) References Cited

OTHER PUBLICATIONS

Mancia et al, "2007 Guidelines for the management of arterial hypertension," European Heart Journal, vol. 28, pp. 1462-1536 (2007).
Monyer et al, "Morphinans attenuate cortical neuronal injury induced by glucose deprivation in vitro," Brain Research, vol. 446, pp. 144-148 (1988).
Mounier-Vehier et al, "Compliance and Antihypertensive Efficacy of Amlodipine Compared With Nifedipine Slow-Release," American Journal of Hypertension, vol. 11, pp. 478-486 (1998).
Nelson et al, "Self-reported adherence with medication and cardiovascular disease outcomes in the Second Australian National Blood Pressure Study (ANBP2)," Medical Journal of Australia, vol. 185, No. 9, pp. 487.
O'Connor, "Improving Medication Adherence: Challenges for Physicians, Payers, and Policy Makers," Archives of Internal Medicine, vol. 166, pp. 1802-1804 (Sep. 25, 2006).
Ong et al, "Prevalence, Awareness, Treatment, and Control of Hypertension Among United States Adults 1999-2004," Hypertension, vol. 49, pp. 69-75 (2007).
Packer et al, "Effect of amlodipine on morbidity and mortality in severe chronic heart failure," The New England Journal of Medicine, vol. 335, No. 15, pp. 1107-1114 (Oct. 10, 1996).
Prince et al, "Dextromethorphan protects against cerebral infarction in a rat model of hyoxia-ischemia," Neuroscience Letters, vol. 85, pp. 291-296 (1988).
Qian et al. Preservation of Ca2+/CAM PK II by two types of calcium channel antagonists in cerebral ischemia. Zhongguo Yingyong Shenglixue Zazhi 14(1 ), pp. 1-4 (1998).
Staessen et al, "Randomised double-blind comparison of placebo and active treatment for older patients with isolated systolic hypertension," Lancet, vol. 350, pp. 757-764 (Sep. 13, 1997).
Steinberg et al, "Dextromethorphan protects against cerebral injury following transient focal ischemia in rabbits," Stroke, vol. 19, pp. 1112-1118 (1988).
Sun et al, Chinese Journal of Neurosurgery, vol. 11 Suppl., pp. 78-79 (Dec. 1995).
The ALLHAT Officers and Coordinators for the ALLHAT Collaborative Research Group, "Major Outcomes in High-Risk Hypertensive Patients Randomized to Angiotensin-Converting Enzyme Inhibitor or Calcium Channel Blocker vs. Diuretic," Journal of the American Medical Association, vol. 288, No. 23, pp. 2981-2996 (Dec. 18, 2002).
Tortella et al, "Dextromethorphan and neuromodulation: old drug coughs up new activities," Trends in Pharmacological Sciences, vol. 10, pp. 501-507 (Dec. 1989).
Tortella et al, "Neuroprotection (Focal Ischemia) and Neurotoxicity (Electroencephalographic) Studies in Rats with AHN649, a 3-Amino Analog of Dextromethorphan and Low-Affinity N-Methyl-D-Aspartate Antagonist," Journal of Pharmacology and Experimental Therapeutics, vol. 291, No. 1, pp. 399-408 (1999).
Zhang et al, "Neuroprotective effect of dextromethorphan in the MPTP Parkinson's disease model: role of NADPH oxidase," The FASEB Journal, vol. 18, pp. 589-591 (2004).
Zheng et al, Chinese Pharmacological Bulletin, vol. 22, No. 9, pp. 1079-1083 (Sep. 2006).
Cai et al. ; "Correlation of genetic polymorphism of cytochrome P4502D6 with dextromethorphan oxidative metabolism in Chinese" (With English Abstract) ; Chin J Med Genet ; vol. 17, No. 3 ; Jun. 2000 ; pp. 181-184.
Dickson et al. ; "Compliance with antihypertensive therapy in the elderly: a comparison of fixed-dose combination amlodipine/benazepril versus component-based free-combination therapy" ; American Journal of Cardiovascular Drugs ; vol. 8, No. 1 ; 2008 ; pp. 45-50.
Gojanovic et al. ; "Concomitant calcium entry blockade and inhibition of the renin-angiotensin system: a rational and effective means for treating hypertension" ; Journal of the Renin-Angiotensin-Aldosterone System (JRAAS) ; vol. 9, No. 1 ; Mar. 2008 ; pp. 1-9.
Laurent-Kenesi et al. ; "Influence of CYP2D6-dependent metabolism on the steady-state pharmacokinetics and pharmacodynamics of metoprolol and nicardipine, alone and in combination" ; British Journal of Clinical Pharmacolog ; vol. 36, No. 6 ; May 10, 1993 ; pp. 531-538.
Talakoub et al. ; "Premedication with oral Dextromethorphan reduces intra-operative Morphine requirement" ; Journal of Research in Medical Sciences ; vol. 10, No. 5 ; Sep.&Oct. 2005 ; pp. 281-284.
Xue et al. ; "Microglia: in inflammation-medicated neurodegenerative diseases" (With English Abstract) ; Chinese Bulletin of Life Sciences ; vol. 19, No. 1 ; Feb. 2007 ; pp. 43-46.
Yamashita et al. ; "Preoperative oral dextromethorphan attenuated tourniquet-induced arterial blood pressure and heart rate increases in knee cruciate ligament reconstruction patients under general anesthesia" ; Anesth. Analg. ; Vo. 98 ; 2004 ; pp. 994-998.
Yang et al. ; "The Mechanism of Dopamine D5 Receptor Regulation Hypertension via NADPH Oxidase" (With English Abstract) ; Chinese Journal of Comparative Medicine ; vol. 16, No. 3 ; Mar. 2006 ; pp. 129-134.
Zheng et al. ; "Role of NADPH oxidase in oxidative stress involved in spontaneously hypertensive rats" (With English Abstract) ; Chinese Pharmacological Bulletin ; vol. 22, No. 9 ; Sep. 2006 ; pp. 1079-1083.

Fig. 2b
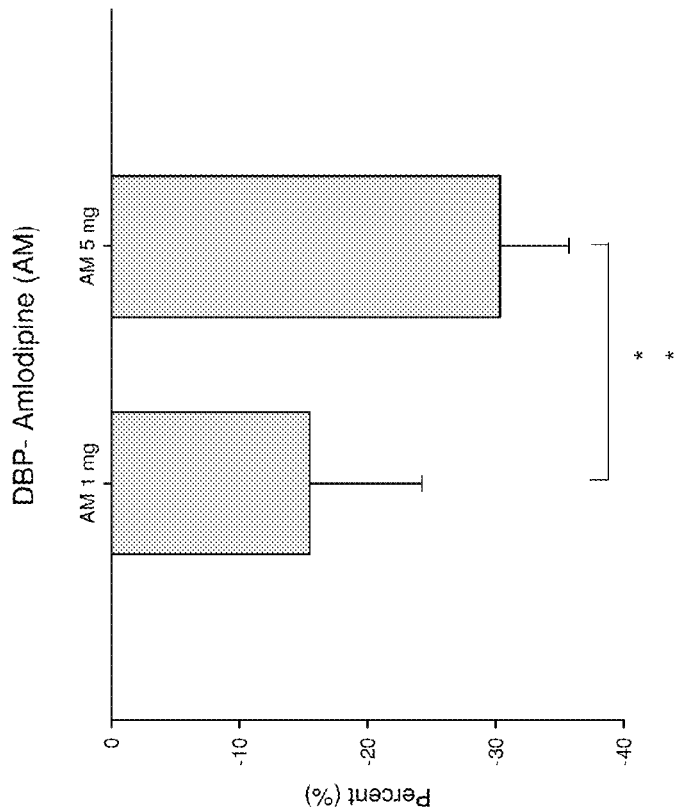
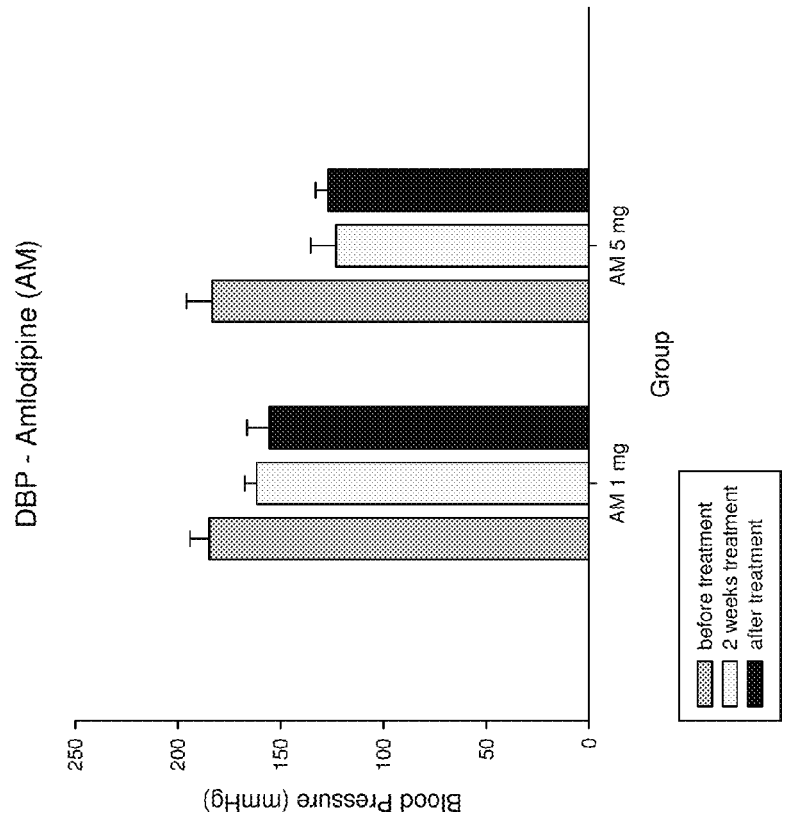

Fig. 2c
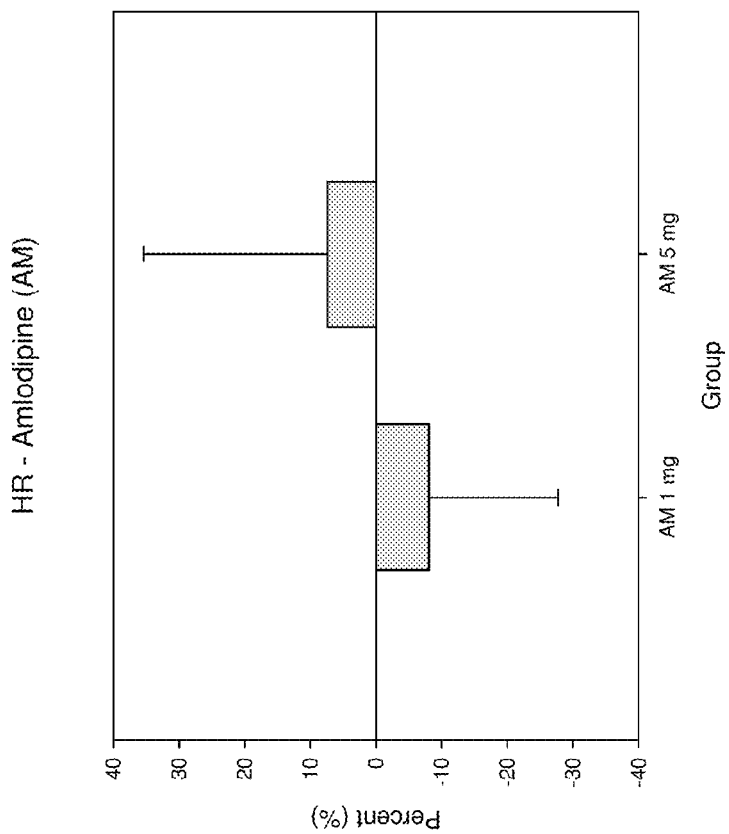
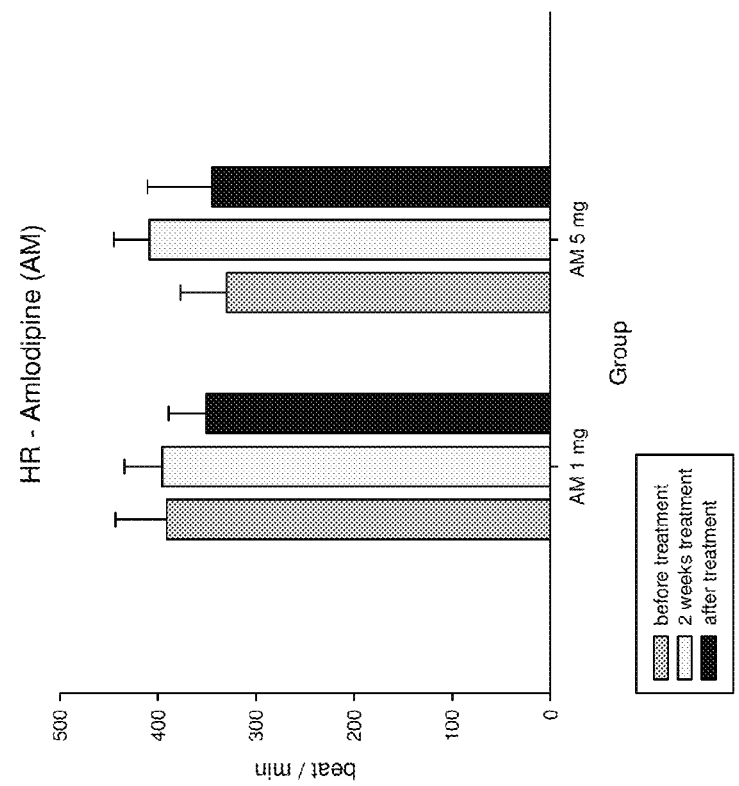

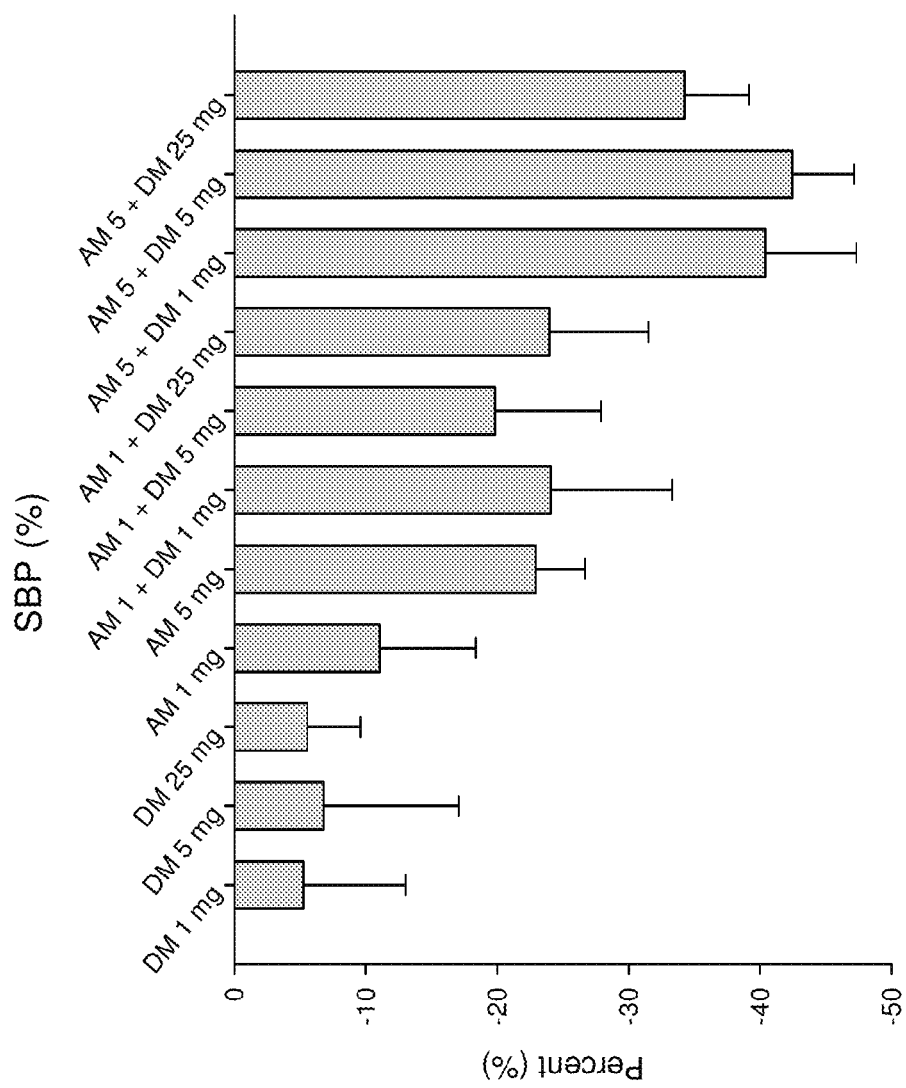

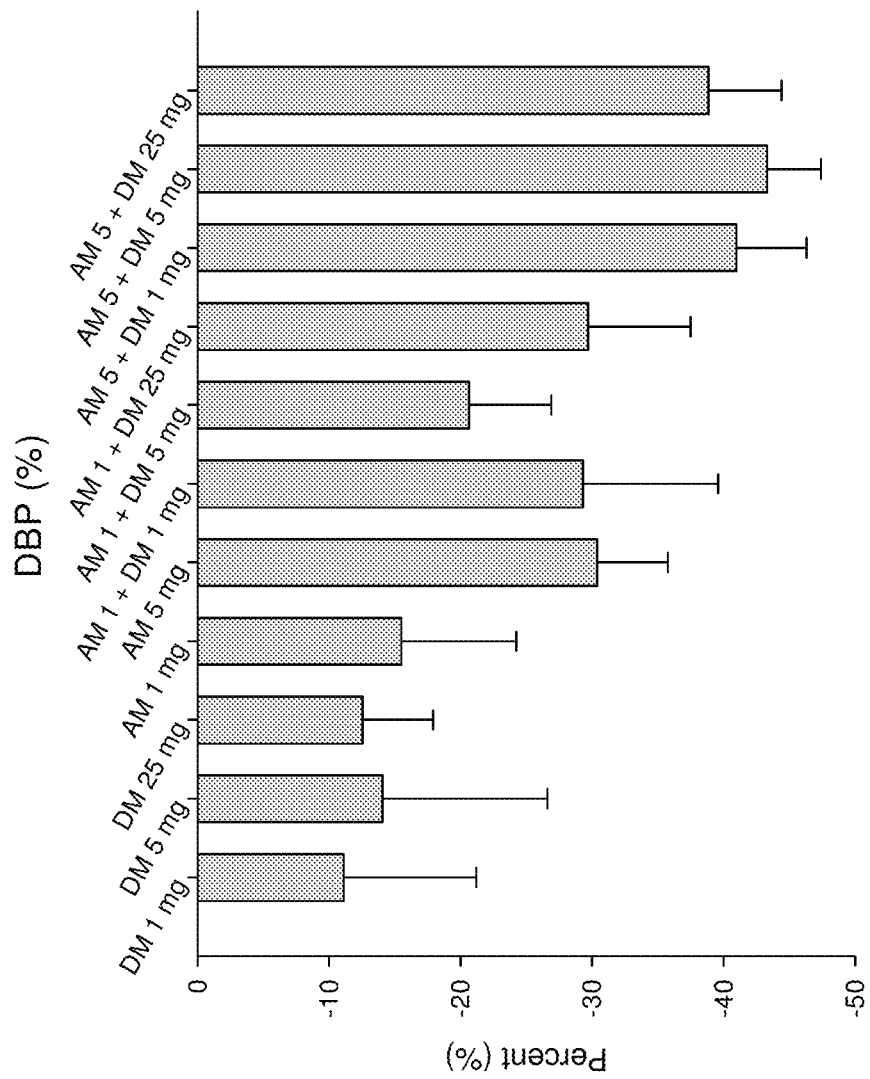

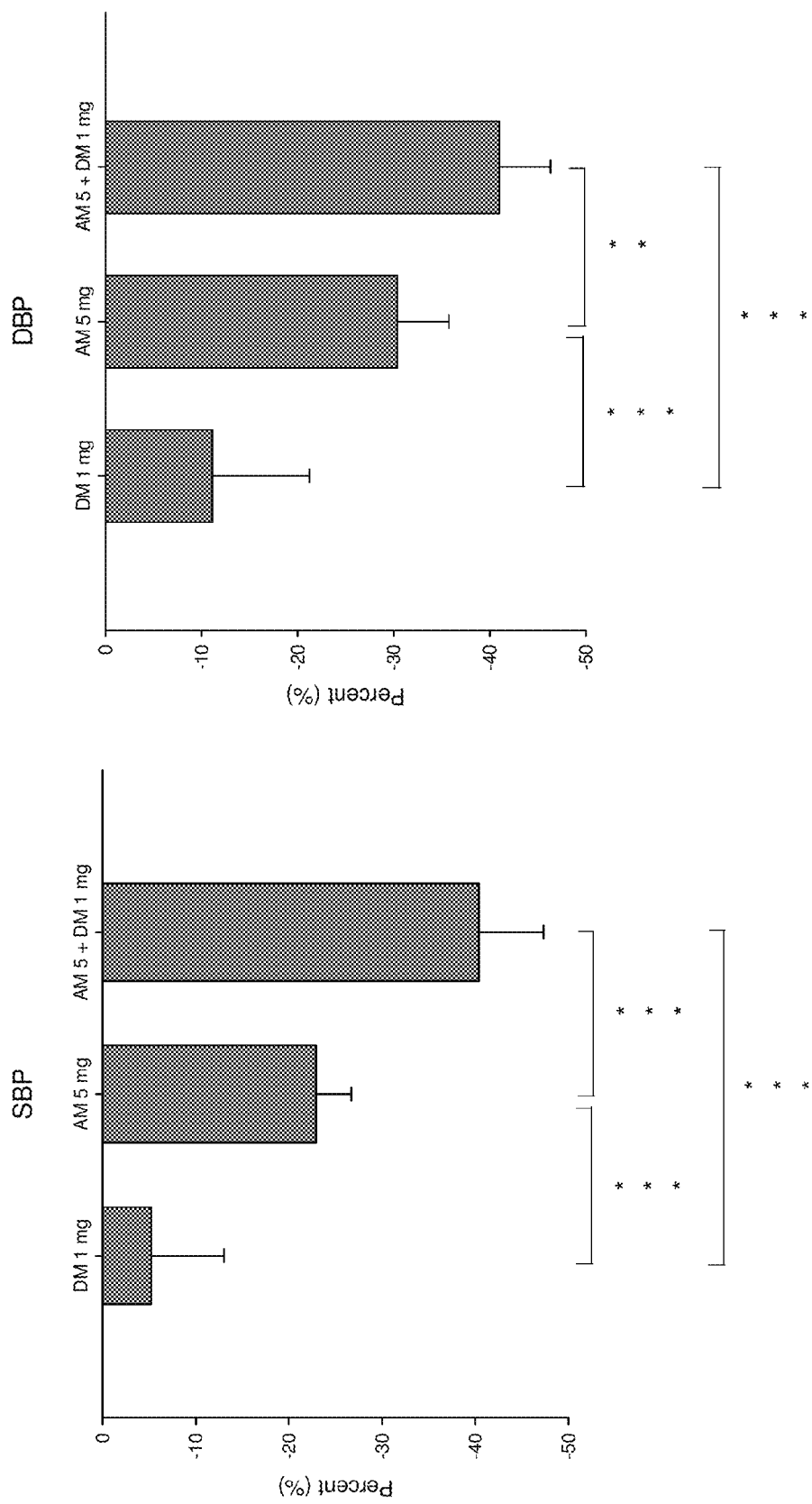

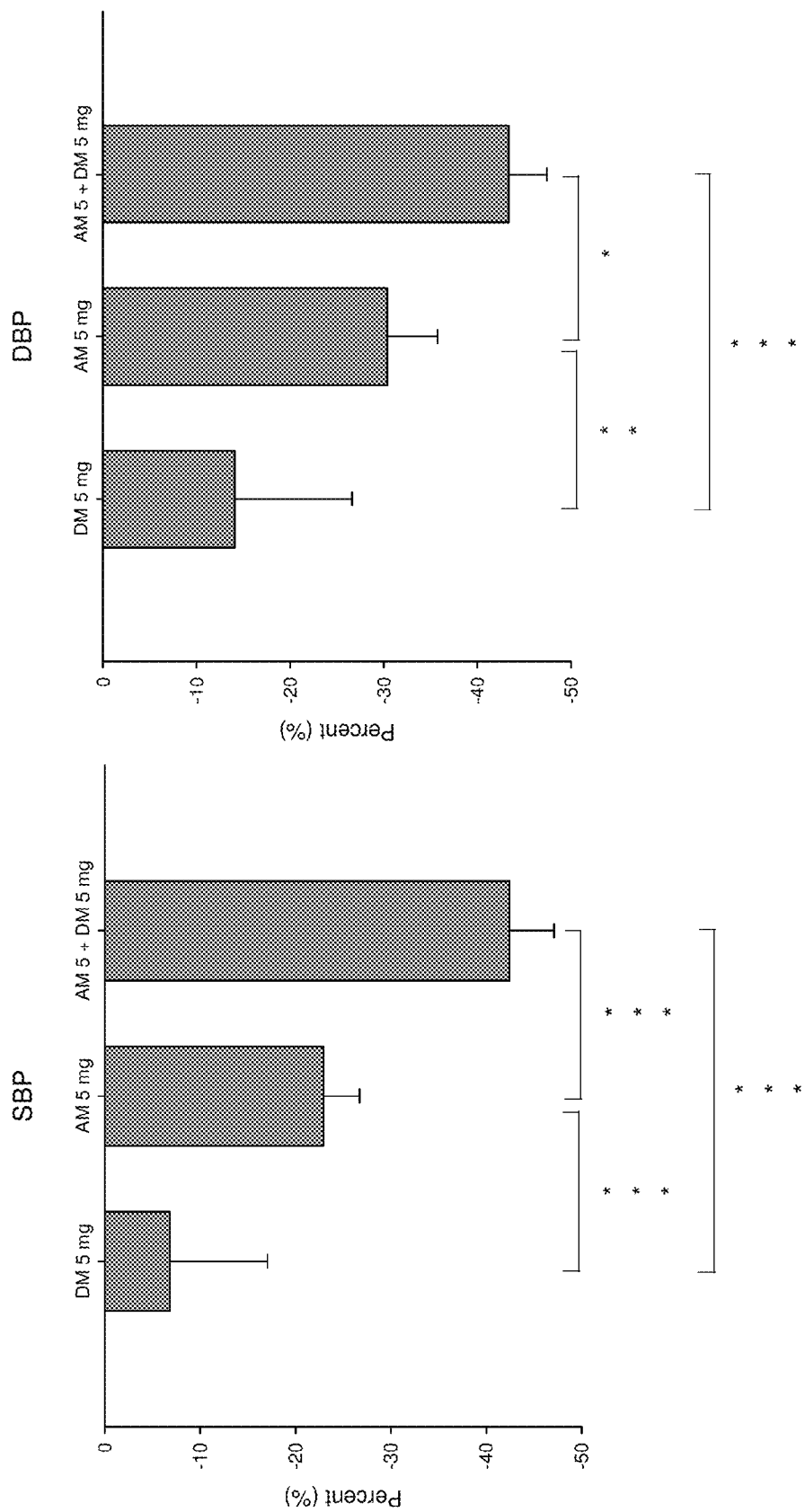

METHOD FOR TREATING HYPERTENSION

This application is a divisional of U.S. application Ser. No. 13/695,628, filed Nov. 1, 2012; which is a 371 National Stage of International Application PCT/CN2011/073560, filed Apr. 29, 2011; which claims priority of U.S. Provisional Application No. 61/330,540, filed May 3, 2010. The contents of the above-identified applications are incorporated herein by reference in their entireties.

BACKGROUND OF THE INVENTION

Hypertension is a public health problem that affects more than 25% of the adult population worldwide. [1,2] Hypertension has been identified as the leading risk factor for mortality and ranks as the third-leading cause of disability-adjusted life-years. [1,3] Despite the availability of numerous antihypertensive agents, the diagnosis, management, and control of hypertension are far from ideal, with control rates of 6% to 30% in different communities worldwide. [1] Nonadherence to antihypertensive treatment has been associated with lower rates of blood pressure (BP) control and higher rates of cardiovascular events. [4-6] Administration of a once-daily fixed-dose combination (FDC) therapy with >2 classes of antihypertensive agents is a strategy adopted for improving adherence and BP control. This strategy has been described in the recent guidelines, even as an initial therapeutic option. [7,8]

NADPH oxidases have recently been shown to contribute to the pathogenesis of hypertension. See Williams et al., 2007, *J. Cardiovasc Pharmacol.*, 50:9-16 and references therein. It has been suggested that specific inhibitors of these enzymes may have potential therapeutic use in hypertensive disease. Two of the most specific inhibitors, gp91ds-tat and apocynin, have been shown to decrease blood pressure in animal models of hypertension. Other inhibitors, including diphenylene iodonium, aminoethyl benzenesulfono fluoride, S17834, PR39, protein kinase C inhibitors, and VAS2870, have shown promise in vitro, but their in vivo specificity, pharmacokinetics, and effectiveness in hypertension remains to be determined. The currently available antihypertensive agents, angiotensinconverting enyzme inhibitors and angiotensin receptor blockers also effectively inhibit NADPH oxidase activation. Similarly, the cholesterol-lowering agents, statins, have been shown to attenuate NADPH oxidase activation.

Dextromethorphan (DM) is a dextrorotatory morphinan and is widely used as a nonopioid cough suppressant in a variety of over-the-counter remedies. [17] It is an NMDA receptor antagonist. The exact mechanism of action of its antitussive activity, however, remains unclear. Studies using animal models of cerebral ischemia and hypoglycemic neural injuries have demonstrated that DM possesses neuroprotective activity. [18-23] DM effectively inhibited the 1-methyl-4-phenyl-1,2,3,6-tetrahydropyridine (MPTP)-induced production of reactive oxygen species (ROS). The neuroprotective effect of DM depended on the normal function of NADPH oxidase.[24] Recent in vitro and in vivo studies showed that DM reduces oxidative stress and inhibits atherosclerosis and neointima formation in mice through the direct inhibition of NADPH oxidase and that it also decreases superoxide production in the aorta and carotid artery of apolipoprotein E (apoE)-deficient mice. Liu et al., 2009, *Cardiovascular Research*, 82:161-169. Alvarez Y et al suggest that the increased production of superoxide anion ($O_2^-$) from NADP(H) oxidase in vessels of hypertensive rats contributes to the vasoconstrictor responses and counteracts the increase of NO from iNOS and the consequent modulation of these responses. [25]

Calcium channel blockers (CCBs) are indicated as initial therapy for hypertension. Their benefits and the possible risks have been explored in several clinical trials. [9-14] Use of high-dose CCBs has been associated with a high incidence of adverse events (AEs), such as peripheral edema and constipation. [8,11,12]

Amlodipine is a CCB with antihypertensive properties prescribed as monotherapy. It is one of a series of dihydropyridine calcium antagonists. It has been found to be well tolerated even in high-risk patients, such as those with coronary disease, heart failure, or multiple risk factors for cardiovascular events. [12-16] Amlodipine has a generally slower onset and longer duration of action than, for example, nifedipine. (Jensen, H. et al., *J. Hum. Hypertens.*, 42(S): 541-45, 1990). The metabolites of amlodipine apparently do not possess significant calcium channel blocking activity, while the parent drug offers a biological half-life of some 35-40 hours, prompting a once-daily dosage regimen. (Lorimer, A. R., et al., *J. Hum. Hypertens.*, 3(3): 191-96, 1989; Glasser, S. F. et al., *AJH*, 2(3): 154-57, 1989). Its ability to block, calcium channels in smooth muscle produces peripheral vasodilation resulting in decreases in both systolic and diastolic blood pressure. The racemic mixture of amlodipine is presently used primarily as an antihypertensive agent, which produces peripheral vasodilation, resulting in decreases in both systolic and diastolic blood pressure when used as an antihypertensive agent. This antihypertensive effect occurs in the relative absence of significant or sustained effects on cardiac rate. However, the administration of the racemic mixture of amlodipine to a human has been found to cause adverse effects, such as edema of the extremities, peripheral edema, headache, flushing/hot flashes, fatigue, vertigo, muscle cramps and dizziness.

There remains a need of novel effective and safe methods and pharmaceutical compositions for treating or preventing hypertension and related symptoms. Such methods and pharmaceutical compositions are described in the present application.

SUMMARY OF THE INVENTION

It is now discovered that dextromethorphan not only is effective to lower blood pressure in a subject suffering from hypertension, but also acts synergistically with a calcium channel blocker to result in a major improvement in the treatment of hypertension, with no or little adverse effects.

In one general aspect, embodiments of the present invention relate to a method of treating hypertension or a symptom associated therewith in a subject. The method comprises administering to the subject a pharmaceutical composition comprising an effective amount of dextromethorphan and a pharmaceutically acceptable carrier.

In one general aspect, embodiments of the present invention relate to a method of treating hypertension or a symptom associated therewith in a subject. The method comprises administering to the subject an effective amount of dextromethorphan and an effective amount of a calcium channel blocker.

In another general aspect, embodiments of the present invention relate to a pharmaceutical composition for treating hypertension or a symptom associated therewith in a subject, comprising an effective amount of dextromethorphan, an effective amount of a calcium channel blocker, and a pharmaceutically acceptable carrier.

In a preferred embodiment, the present invention relates to a pharmaceutical composition for treating hypertension or a symptom associated therewith in a subject, which comprises an effective amount of dextromethorphan, an effective amount of amlodipine, and a pharmaceutically acceptable carrier.

In another general aspect, embodiments of the present invention relate to a pharmaceutical composition for treating hypertension or a symptom associated therewith in a subject, comprising an effective amount of a calcium channel blocker, an effective amount of a NADPH oxidase inhibitor, and a pharmaceutically acceptable carrier.

Other aspects of the present invention relate to methods of treating hypertension or a symptom associated therewith in a subject, comprising administering to the subject an effective amount of a calcium channel blocker, such as amlodipine, and an effective amount of a NADPH oxidase inhibitor, such as dextromethorphan.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1a: changes of systolic blood pressure (SBP) after DM treatment;

FIG. 1b: changes of diastolic blood pressure (DBP) after DM treatment;

FIG. 1c: changes of heart rate (HR) after DM treatment; and

FIG. 1d: changes of mean blood pressure (MBP) after DM treatment;

FIGS. 2a-2d illustrate the blood pressure lowing effect of amlodipine (AM) in SHR, at two dosage levels, 1 mg/kg/day and 5 mg/kg/day:

FIG. 2a: changes of SBP after AM treatment;
FIG. 2b: changes of DBP after AM treatment;
FIG. 2c: changes of HR after AM treatment; and
FIG. 2d: changes of MBP after AM treatment;

FIG. 3a: changes of SBP after DM+AM treatment;
FIG. 3b: changes of DBP after DM+AM treatment;
FIG. 3c: changes of HR after DM+AM treatment; and
FIG. 3d: changes of MBP after DM+AM treatment;

FIGS. 4a-4d illustrate the blood pressure lowing effect of different treatment regimens in SHR, expressed as percentage change of blood pressure or heart rate:

FIG. 4a: percentage changes of SBP after different treatment regimens;

FIG. 4b: changes of DBP after different treatment regimens;

FIG. 4c: changes of HR after different treatment regimens; and

FIG. 4d: changes of MBP after different treatment regimens;

FIGS. 5a and 5b show the comparison of blood pressure lowering effect of single and combination treatments in SHR as percentage changes of SBP and DBP:

FIG. 5a: percentage changes of SBP and DBP after single treatment with DM at 1 mg/kg/day, single treatment with AM at 5 mg/kg/day, and combined treatment with DM at 1 mg/kg/day and AM at 5 mg/kg/day; and FIG. 5b: percentage changes of SBP and DBP after single treatment with DM at 5 mg/kg/day, single treatment with AM at 5 mg/kg/day, and combined treatment with DM at 5 mg/kg/day and AM at 5 mg/kg/day;

DETAILED DESCRIPTION OF THE INVENTION

Figure 1A:
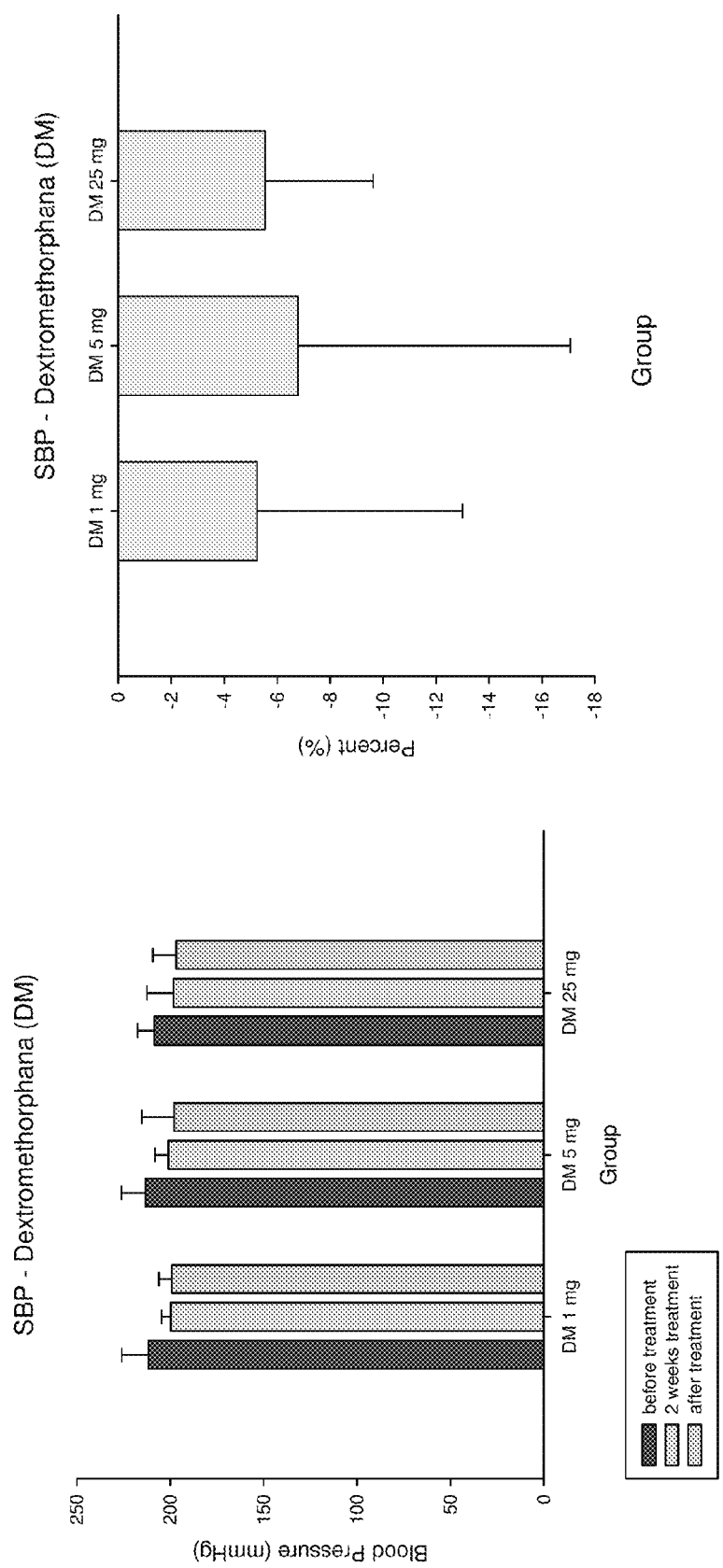
FIGS. 1a-1d illustrate the blood pressure lowing effect of dextromethorphan (DM) in an animal model for hypertension, i.e., spontaneous hypertensive rats (SHR), at three dosage levels, 1 mg/kg/day, 5 mg/kg/day, and 25 mg/kg/day.
Figure 1B:
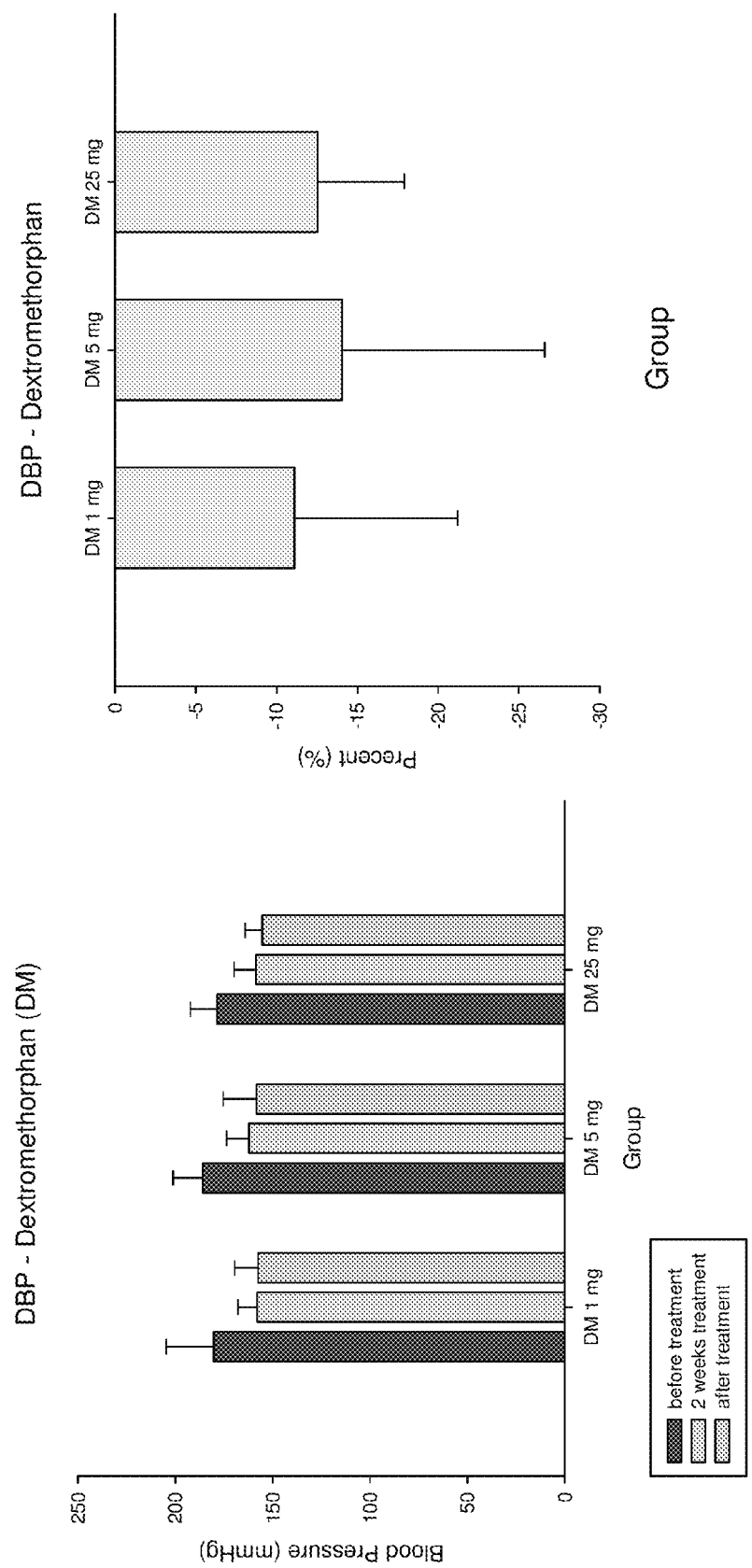
Figure 1C:
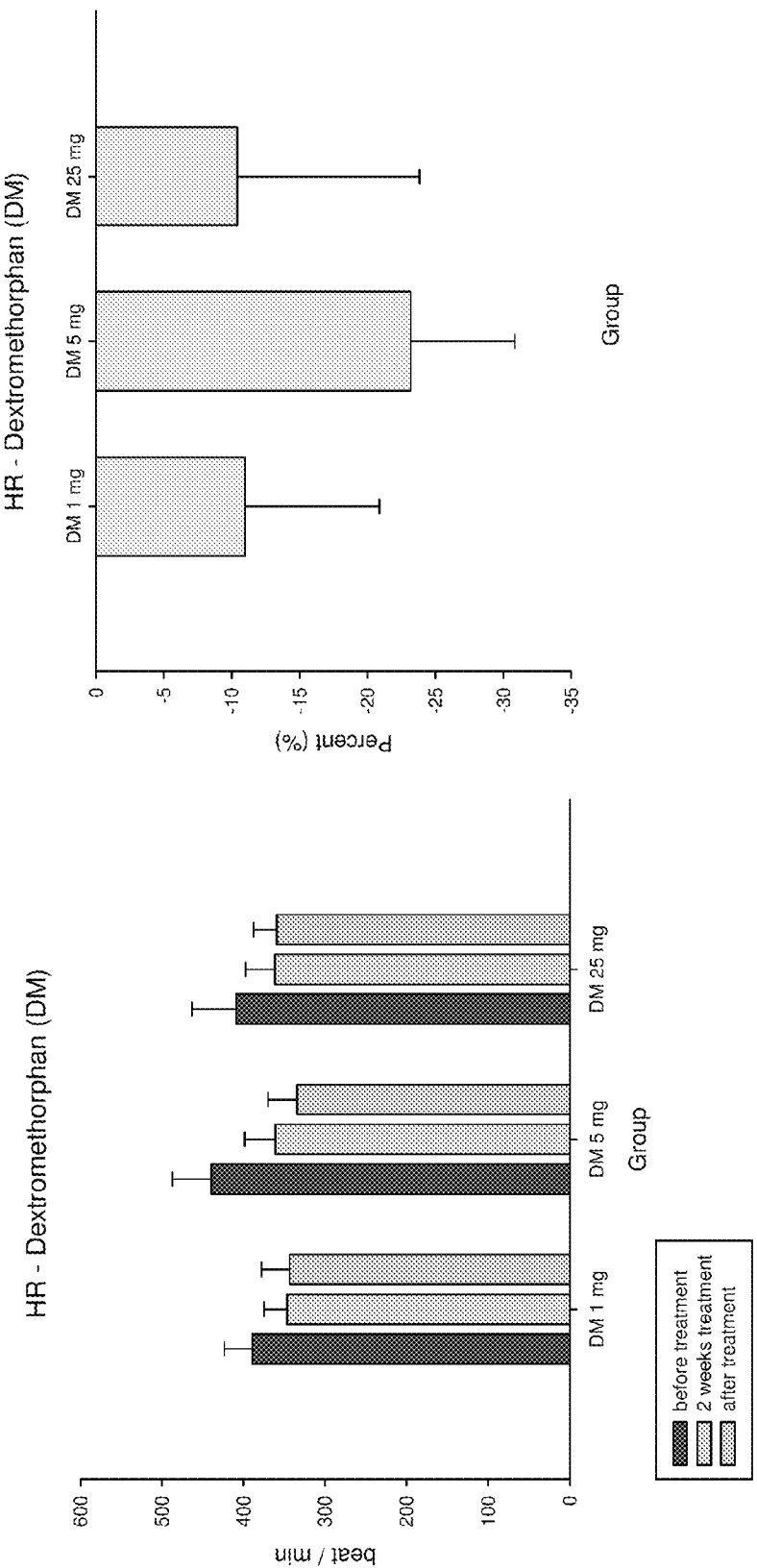
Figure 1D:
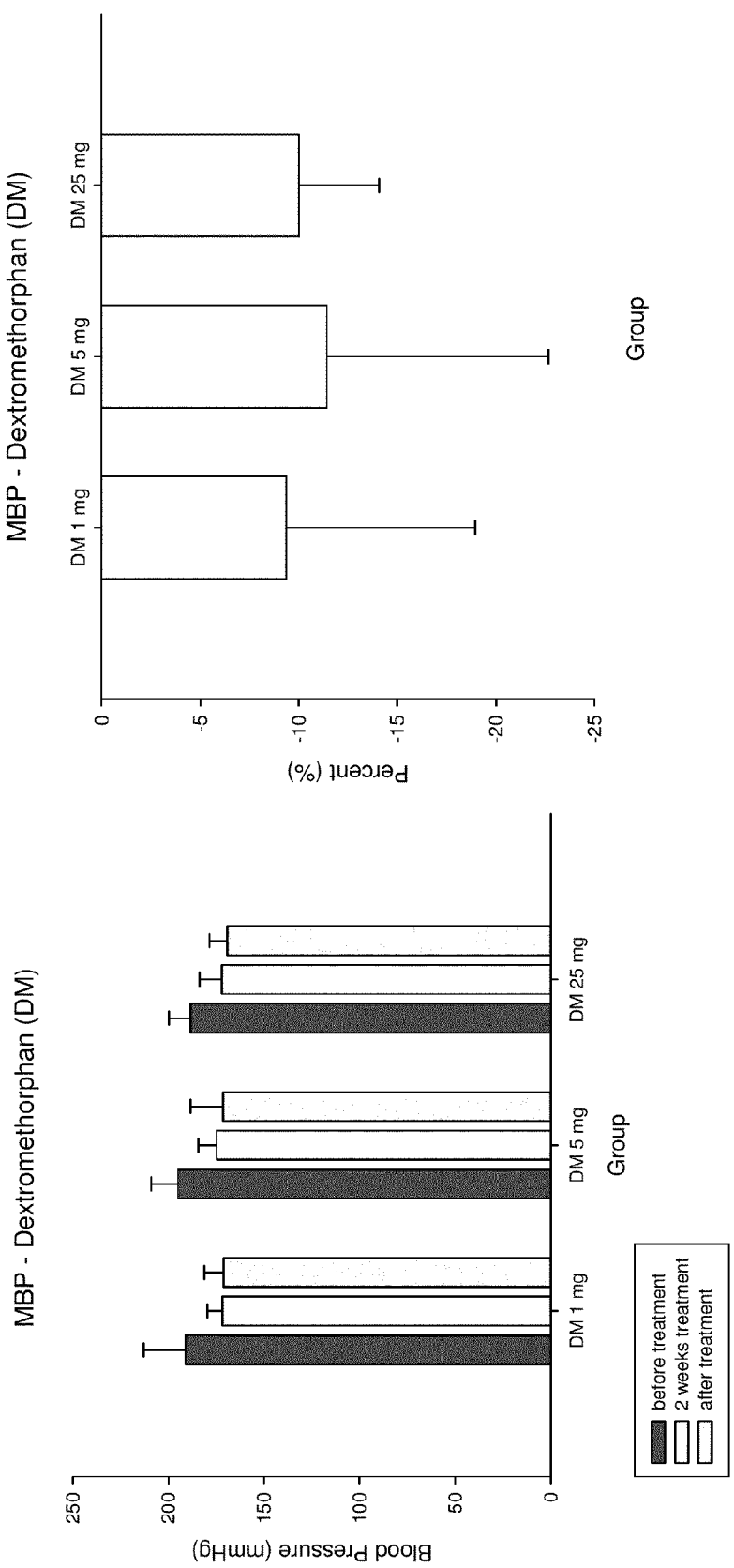
Figure 2A:
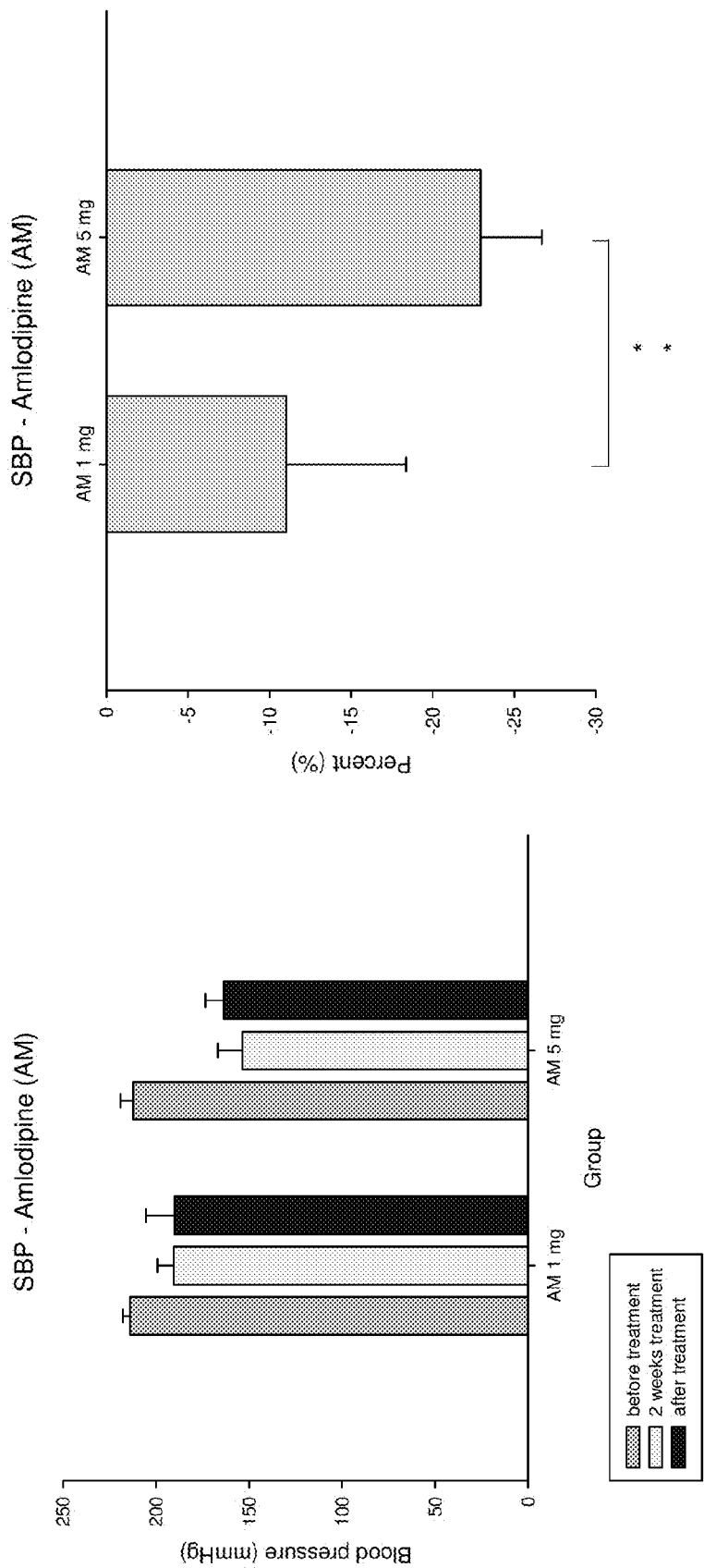
Figure 2D:
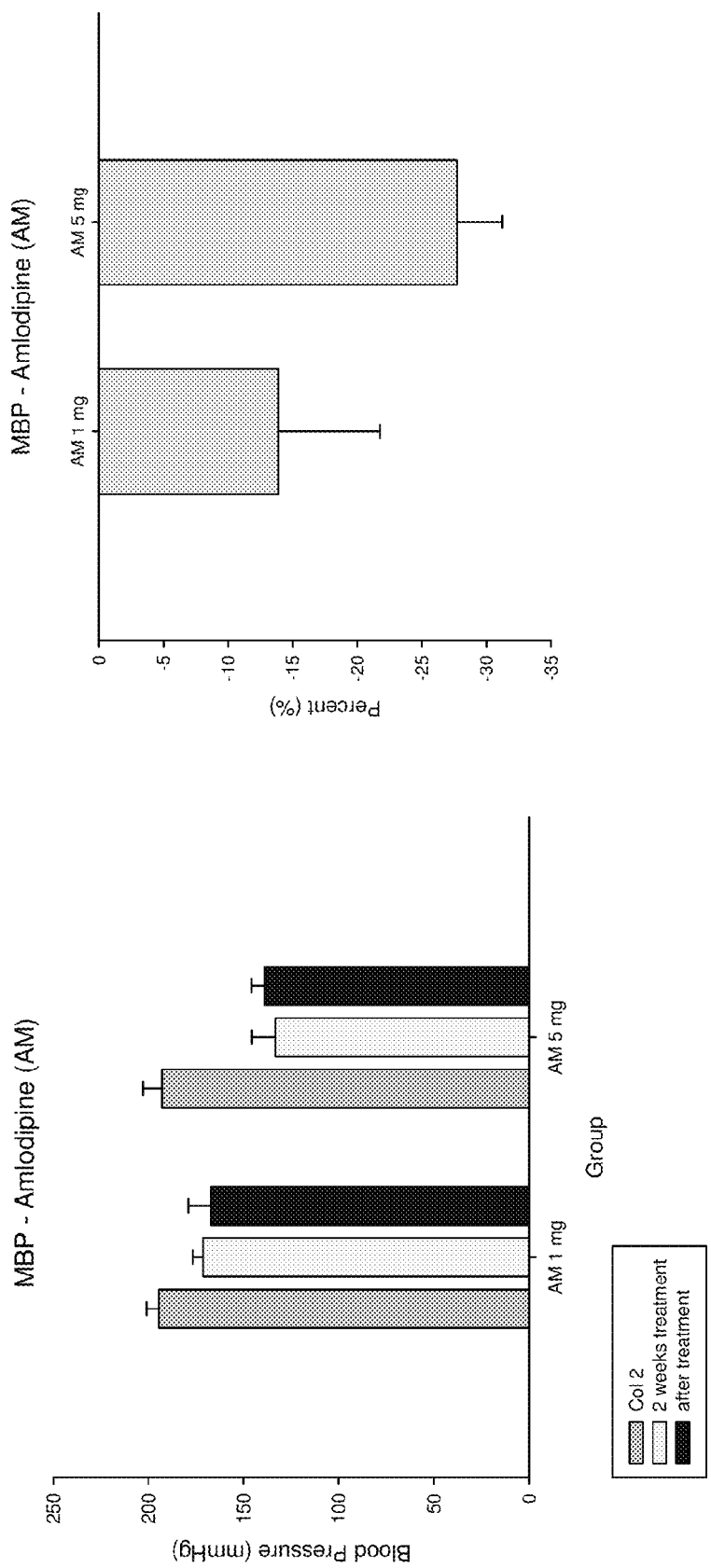
Figure 3A:
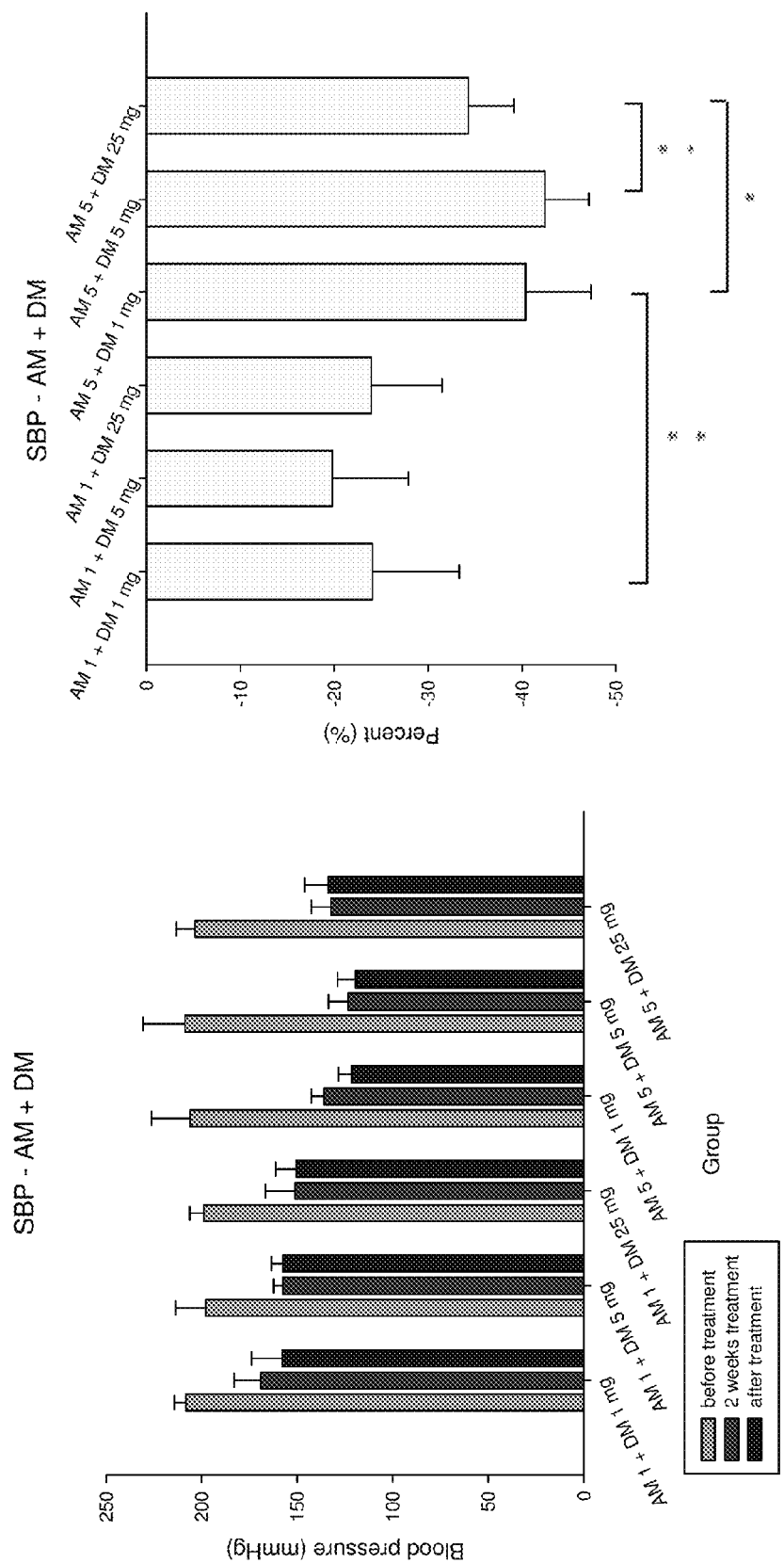
FIGS. 3a-3d illustrate the blood pressure lowing effect of the combination of DM and AM in SHR, at various dosage levels.
Figure 3B:
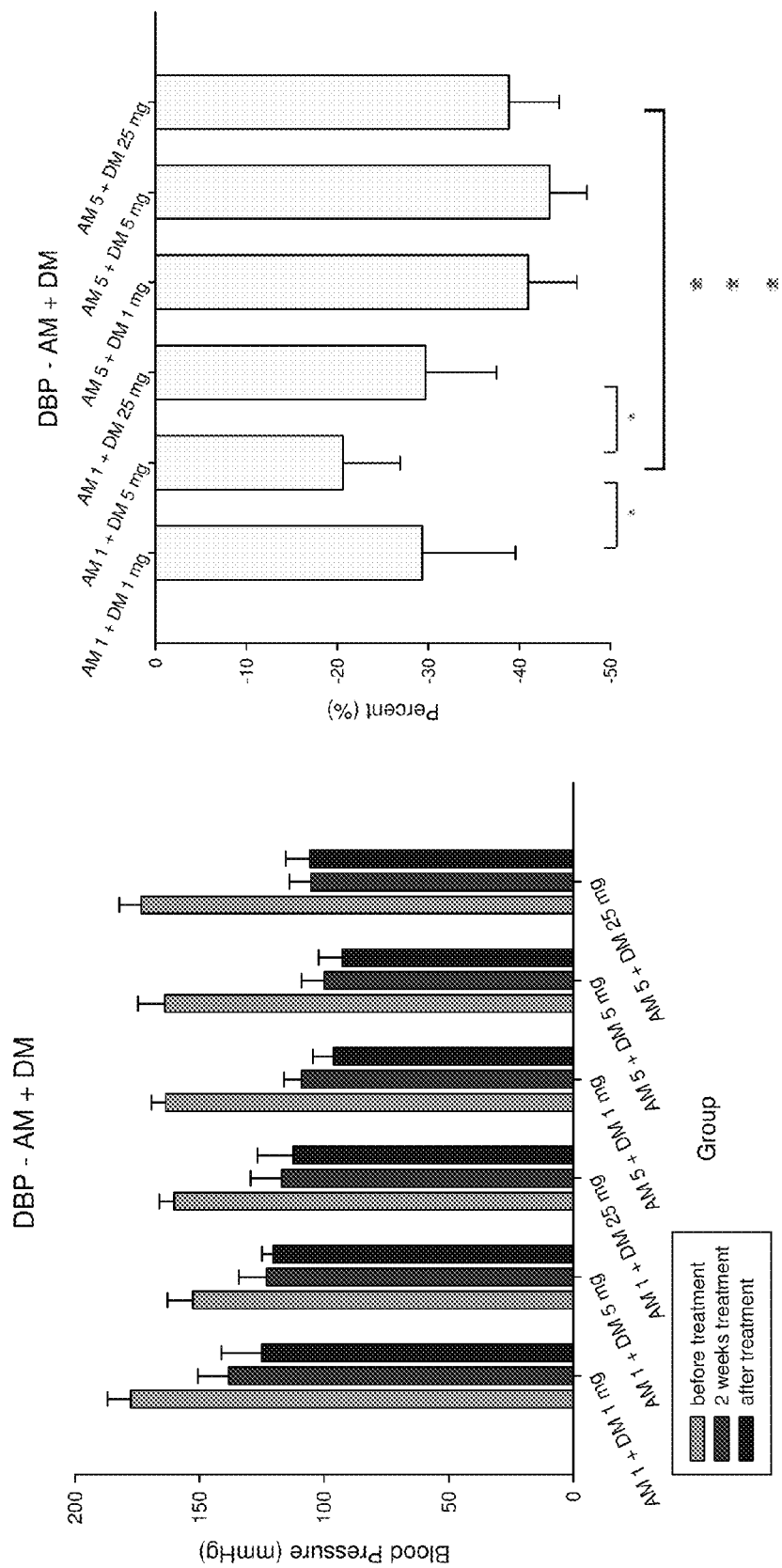
Figure 3C:
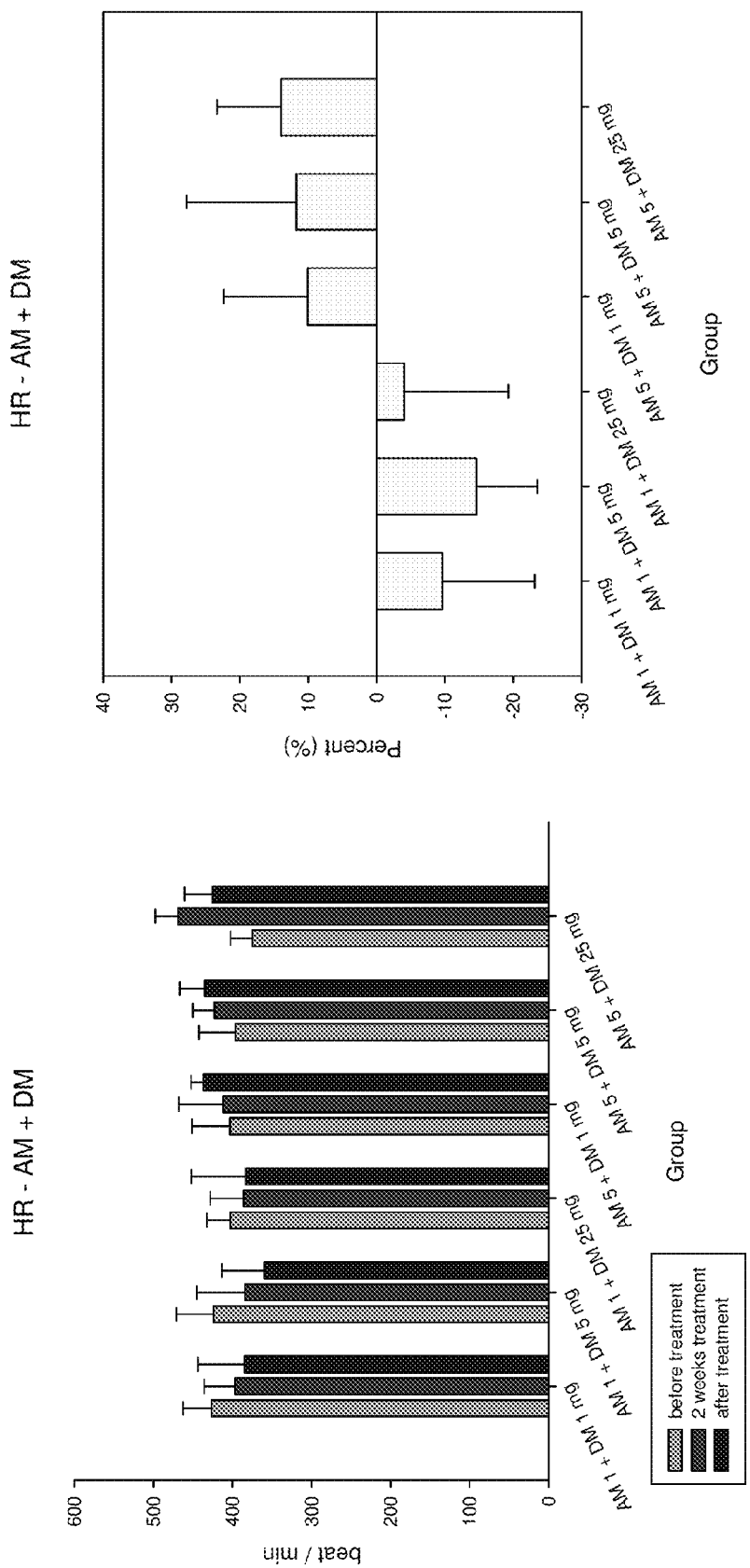
Figure 3D:
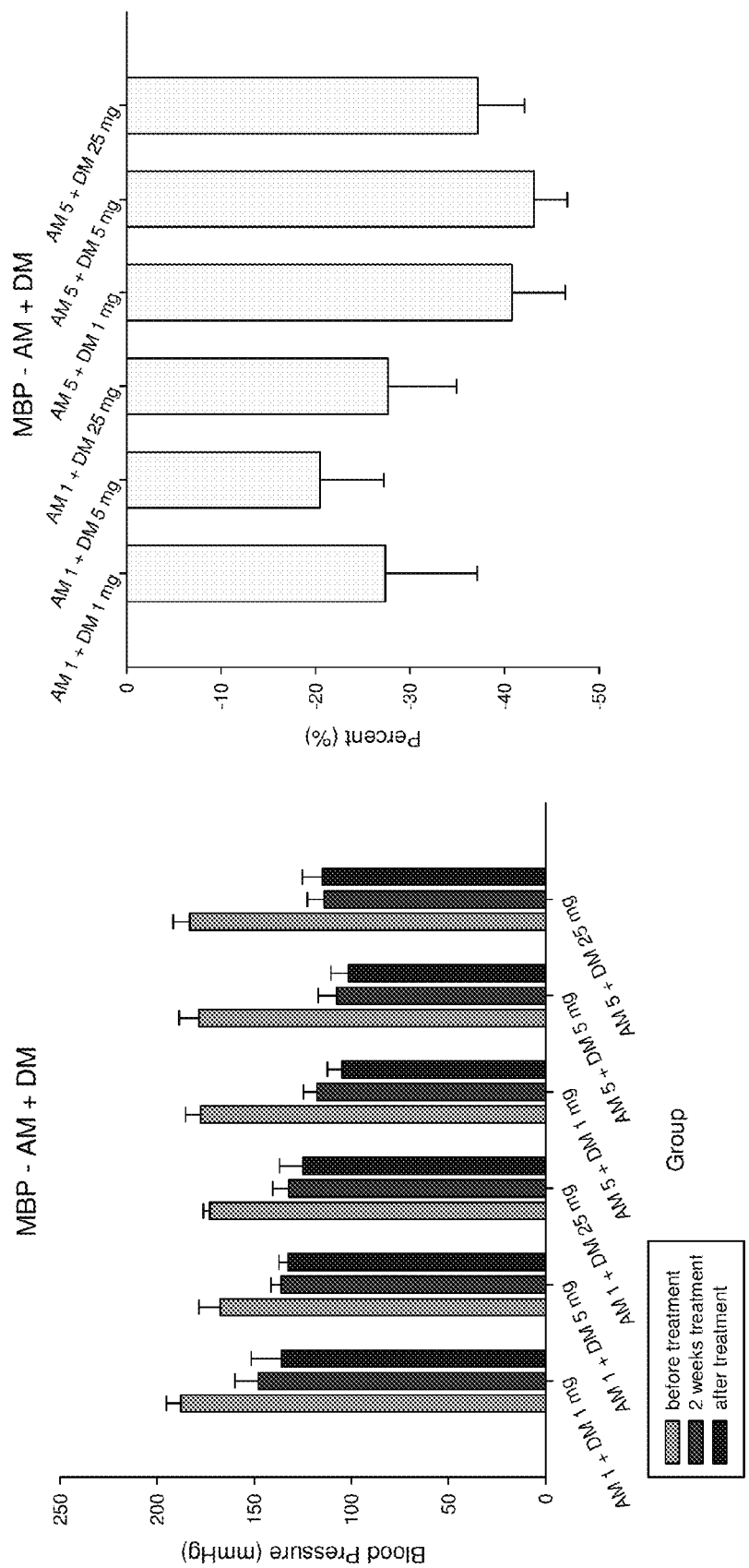
Figure 4C:
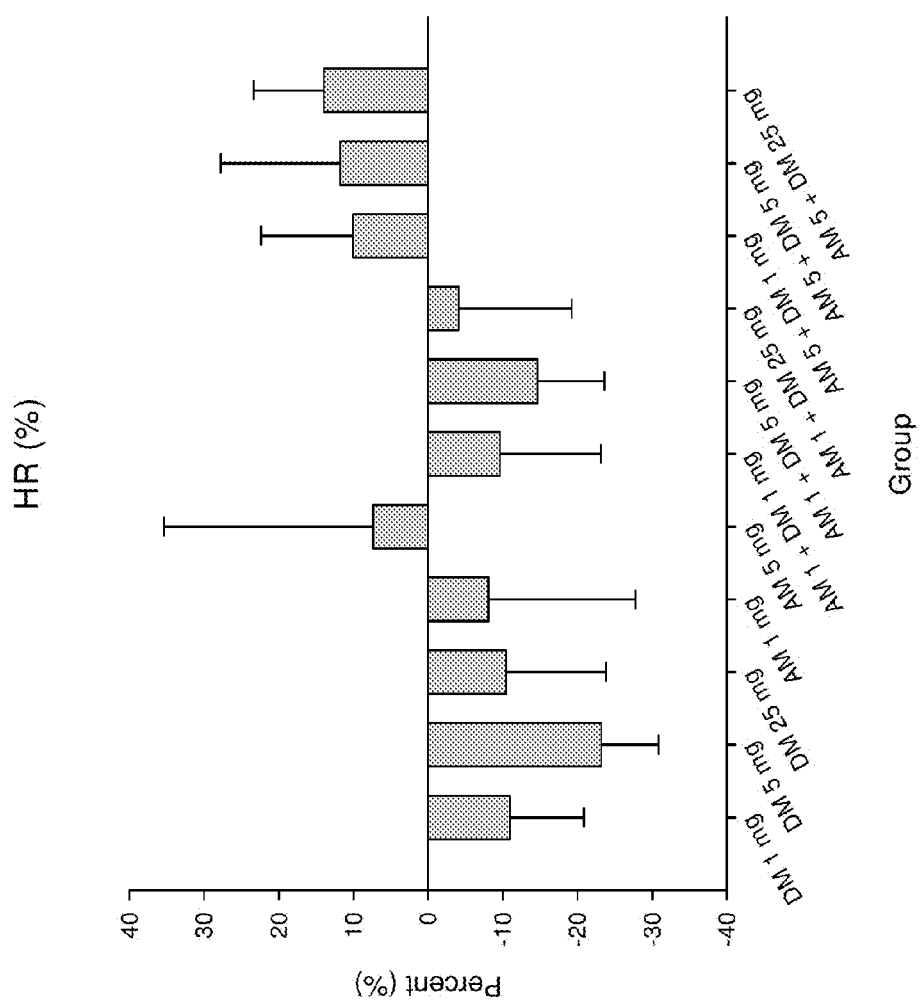
Figure 4D:
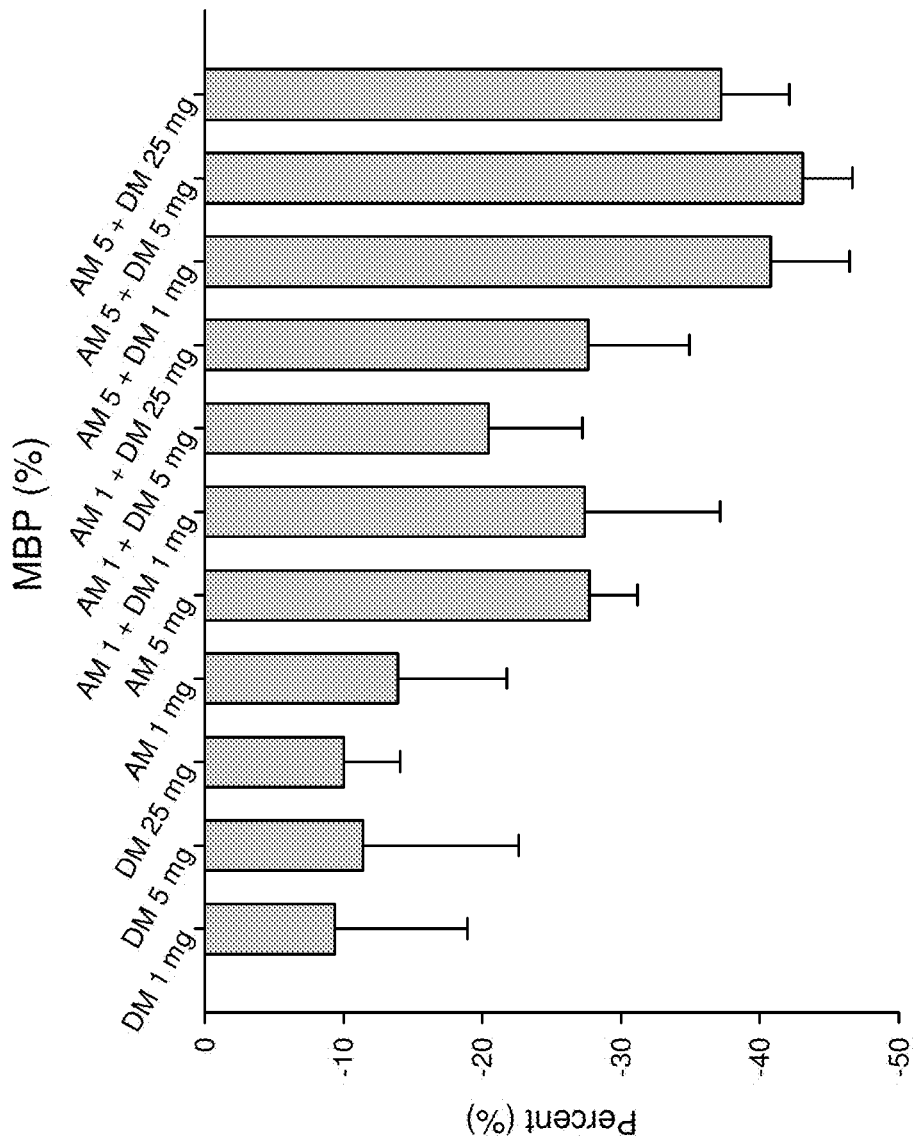

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the name of a compound, such as dextromethorphan or amlodipine, can encompass all possibly existing isomeric forms (e.g., optical isomer, enantiomer, diastereomer, racemate or racemic mixture), esters, prodrugs, metabolite forms, pharmaceutically acceptable salts, pharmaceutically acceptable esters, pharmaceutically acceptable amides, and protected derivatives, of the compound.

The phrase "pharmaceutically acceptable salt(s)", as used herein, means those salts of a compound of interest that are safe and effective for pharmaceutical use in mammals and that possess the desired biological activity. Pharmaceutically acceptable salts include salts of acidic or basic groups present in the specified compounds. The acidic or basic groups can be organic or inorganic. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, and diethanolamine salts. Certain compounds used in the present invention can form pharmaceutically acceptable salts with various amino acids, e.g., lysine, N,N'-dibenzylethylenediamine, chloroprocaine, choline, diethanolamine, ethylenediamine, meglumine (N-methylglucamine), procaine, and tris, and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. For a review on pharmaceutically acceptable salts see BERGE ET AL., 66 *J. PHARM. SCI.* 1-19 (1977), incorporated herein by reference.

As used herein, a "NADPH oxidase inhibitor" is a drug or a natural substance that inhibits, decreases or reduces the enzymatic activity of a NADPH oxidase, i.e., nicotinamide adenine dinucleotide phosphate-oxidase. The NADPH oxidase generates superoxide by transferring electrons from NADPH and coupling the electrons to molecular oxygen to produce superoxide, a reactive free-radical that can generate reactive oxygen species (ROS). A "NADPH oxidase inhibitor" is effective in preventing, decreasing or reducing the production of the superoxide, thus ROS, in blood vessels of a subject. Examples of NADPH oxidase inhibitors that can be used in the present invention include, but are not limited to, dextromethorphan, gp91ds-tat, apocynin, diphenylene iodonium, aminoethyl benzenesulfono fluoride, S17834, PR39, protein kinase C inhibitors, VAS2870, angiotensin-converting enyzme inhibitors, angiotensin receptor blockers and statins.

As used herein, "dextromethorphan" or "DM" refers to the compound (+)-3-methoxy-17-methyl-9α,13α,14α-morphinan, which is also named (+)-3-methoxy-N-methylmorphinan, and any pharmaceutically acceptable salt thereof. For example, dextromethorphan can be in a pharmaceutically acceptable salt form selected from the group consisting of salts of free acids, inorganic salts, salts of sulfate, salts of hydrochloride, and salts of hydrobromide. Dextromethorphan is commonly available as the monohydrated hydrobromide salt.

Dextromethorphan is the dextrorotatory (d) enantiomer. Preferably, a pharmaceutical composition according to embodiments of the present invention comprises substantially optically pure dextromethorphan or is substantially free of the levorotary (l) enantiomer of DM.

As used herein, "substantially optically pure dextromethorphan" or "substantially free of the levorotary (l) enantiomer of DM" means that the pharmaceutical composition contains a greater proportion or percentage of DM in relation to its l enantiomer. For example, the pharmaceutical composition preferably contains about 90%, 91%, 92%, 93%, 94%, 95%, 96%, 97%, 98%, 99% or 100%, by weight of DM, wherein the percentage is based on the total amount of DM and its l enantiomer in the pharmaceutical composition.

Dextromethorphan can be synthesized and optically purified using methods known in the art, for example as described in U.S. Pat. No. 2,676,177, the content of which is hereby incorporated by reference. It is also available from various commercial sources.

As used herein, "calcium channel blockers" or "CCBs" refers to a class of drugs and natural substances that disrupt the calcium ($Ca^{2+}$) conduction of calcium channels. They block voltage-gated calcium channels (VGCCs) in cardiac muscle and blood vessels and decrease blood pressure. The term "calcium channel blockers" encompasses any class of CCBs that can be used for treating hypertension in a subject, such as the class of dihydropyridine, phenylalkylamine, benzothiazepine, and the nonselective CCBs. Examples of CCBs that can be used in the present invention include, but are not limited to, amlodipine, bepridil, clentiazem, diltiazem, fendiline, gallopamil, mibefradil, prenylamine, semotiadil, terodiline, verapamil, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, perhexiline, and fluspirilene.

As used herein, "amlodipine" or "AM" refers to the compound 3-ethyl 5-methyl 2-[(2-aminoethoxy)methyl]-4-(2-chlorophenyl)-1,4-dihydro-6-m ethylpyridine-3,5-dicarboxylate, and any optical isomer, enantiomer, diastereomer, racemate or racemic mixture, pharmaceutically acceptable salts, or pharmaceutically acceptable esters, of the compound. For example, amlodipine can be in a pharmaceutically acceptable salt form of inorganic and organic acids. Such acids are selected from the group consisting of acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. (See Campbell, S. F. et al., U.S. Pat. No. 4,806,557). Amlodipine can also be a pharmaceutically acceptable ester of amlodipine, particularly lower alkyl esters.

Amlodipin is a chiral compound. A pharmaceutical composition according to embodiments of the present invention can comprise a racemate, i.e., 1:1 mixture of (R)-(+)- and (S)-(−)-amlodipine or a racemic mixture of the (R)-(+)- and (S)-(−)-amlodipine at different ratios. The pharmaceutical composition can also comprise isolated (R)-(+)-amlodipine or (S)-(−)-amlodipine that is substantially free of the other stereoisomer.

(S)-(−)-amlodipine is a more potent calcium channel blocker than (R)-(+)-amlodipine. Thus, preferably, a pharmaceutical composition according to embodiments of the present invention comprises substantially optically pure (S)-(−)-amlodipine or is substantially free of (R)-(+)-amlodipine.

As used herein, "substantially optically pure (S)-(−)-amlodipine" or "substantially free of (R)-(+)-amlodipine" means that the pharmaceutical composition contains a greater proportion or percentage of (S)-(−)-amlodipine in relation to (R)-(+)-amlodipine. For example, the pharmaceutical composition preferably contains about 90%, 91%, 92%, 93%, 94%, 95%, 96%, 97%, 98%, 99% or 100%, by weight of (S)-(−)-amlodipine, wherein the percentage is based on the total amount of (R)-(+)-amlodipine and (S)-(−)-amlodipine in the pharmaceutical composition.

The chemical synthesis of the racemic mixture of amlodipine can be performed using methods known in the art, e.g., as described in Arrowsmith, J. E. et al., *J. Med. Chem.*, 29: 1696-1702 (1986). It is also available from various commercial sources. Separation of the amlodipine isomers from the racemic mixture can be performed by methods known in the art, such as those illustrated in U.S. Pat. No. 6,448,275 or U.S. Pat. No. 7,482,464. The contents of the references are hereby incorporated by reference.

As used herein, the term "pharmaceutical composition" is intended to encompass a product or composition comprising the specified ingredient in the specified amount, as well as any product which results, directly or indirectly, from combinations of the specified ingredient in the specified amount.

As used herein, the term "subject" means any animal, preferably a mammal, most preferably a human, to whom will be or has been administered compounds or pharmaceutical compositions according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of, or has been the object of observation or experiment of, treatment or prevention of hypertension and symptoms associated therewith.

As used herein, "treating hypertension or a symptom associated therewith" means to elicit an antihypertensive effect, such as by providing a normalization to otherwise elevated systolic and/or diastolic blood pressure, and by so doing providing relief from one or more possible symptoms or other hemodynamic effects caused by the elevated blood pressure.

In one embodiment, "treating" refers to an amelioration, prophylaxis, or reversal of a disease or disorder, or at least one discernible symptom thereof, for example, treating hypertension or a symptom associated therewith by lowering the elevated systolic and/or diastolic blood pressure.

In another embodiment, "treating" refers to an amelioration, prophylaxis, or reversal of at least one measurable physical parameter related to the disease or disorder being treated, not necessarily discernible symptom in or by the mammal, for example, treating hypertension or a symptom associated therewith by decreasing ROS in the vessels.

In yet another embodiment, "treating" refers to inhibiting or slowing the progression of a disease or disorder, either physically, e.g., stabilization of a discernible symptom, physiologically, e.g., stabilization of a physical parameter, or both.

In yet another embodiment, "treating" refers to delaying the onset of a disease or disorder or reduce of the risk of acquiring a disease or disorder, such as hypertension or a symptom associated therewith. For example, the specified pharmaceutical compositions are administered as a preventative measure to a subject having a predisposition to hypertension, even though symptoms of hypertension are absent or minimal.

As used herein, the term "effective amount" of a compound refers to the amount of the compound that elicits the biological or medicinal response in a tissue system, animal or human that is being sought by a researcher, veterinarian, medical doctor or other clinician, which includes alleviation of the symptoms of the disease or disorder being treated. In a preferred embodiment, the effective amount of a compound is sufficient to treat, improve the treatment of, or prophylactically prevent, hypertension or a symptom associated therewith, but is insufficient to cause significant adverse effects associated with administration of the compound.

Methods are known in the art for determining the effective amount of a therapeutically active ingredient according to embodiments of the present invention. Furthermore, and as is also understood by those of ordinary skill in the art, specific dose levels for any particular subject will depend upon a variety of factors including the age, body weight, general health, sex, diet, time of administration, route of administration, rate of excretion, any additional therapeutic agents administered in combination therewith and the severity of the disease or condition being treated. Generally speaking, the prophylactic or therapeutic treatment of the above identified conditions is expected to be achieved via administration of dosage levels of the active ingredients in amounts from about 0.01 mg/kg to about 100 mg/kg, 0.03 mg/kg to about 75 mg/kg, 0.05 mg/kg to about 50 mg/kg body weight per day, or from about 0.1 mg/kg to about 10 mg/kg of body weight per day. Whatever the desired or appropriate dosage level, it may be administered in a single daily dose, or the total daily dosage may be administered in divided doses of two, three or four times daily. Alternatively, the dosage can be formulated to be delivered in a substantially continuous fashion, as may be provided by sustained and/or controlled release dosage forms, or by a transdermal patch.

The term "adverse effects" includes, but is not limited to, cardiovascular effects (including tachycardia and diminished contractility of the heart), edema of the extremities, headache, dizziness, flushing, fatigue, vertigo, muscle cramps, hallucination, diarrhea, fever, urinary retention, vomiting, body rash/itching, etc.

It is now discovered that dextromethorphan is effective to lower blood pressure in a subject suffering from hypertension, either alone or in combination with another antihypertensive agent. It is further discovered that dextromethorphan, a NADPH oxidase inhibitor, and amlodipine, a CCB, act synergistically in lowering blood pressure in a subject suffering from hypertension. This synergistic effect is unexpected. Novel and more effective pharmaceutical compositions and methods for treating hypertension or a symptom associated therewith are thus developed based on the present discoveries.

In one general aspect, the present invention relates to a method of treating hypertension or a symptom associated therewith in a subject. The method comprises administering to the subject a pharmaceutical composition comprising an effective amount of dextromethorphan and a pharmaceutically acceptable carrier.

Any of the pharmaceutically acceptable salt of dextromethorphan can be used in the pharmaceutical compositions and methods according to embodiments of the present invention. In a preferred embodiment, a substantially optically pure dextromethorphan, such as a substantially optically pure dextromethorphan hydrobromide, is used in the present invention.

In most patients, dextromethorphan is rapidly absorbed from the gastrointestinal tract and converted into the less active metabolite, dextrorphan, in the liver by the cytochrome P450 enzyme CYP2D6. Inhibiting the enzymatic activity of CYP2D6 would increase the stability of dextromethorphan and prolong its half life in the subject, resulting in more effective treatment with more consistent and predictable result.

Thus, a method according to an embodiment of the present invention can further comprise administering to the subject a CYP2D6 inhibitor. Examples of CYP2D6 inhibitors that can be used in the present invention include, but are not limited to, quinidine. The CYP2D6 inhibitors can be administered together with DM in the same pharmaceutical composition, or separately from DM in a different pharmaceutical composition, so long as the dosing schedules of DM and the CYP2D6 inhibitor overlap in time so that the administered CYP2D6 inhibitor is effective to prolong the half life of dextromethorphan in the subject.

In another general aspect, embodiments of the present invention relate to a method of treating hypertension or a symptom associated therewith in a subject, comprising administering to the subject an effective amount of dextromethorphan and an effective amount of a calcium channel blocker (CCB).

Any of the CCBs effective for treating hypertension in a subject can be used in the present invention, including, but not limited to, amlodipine, bepridil, clentiazem, diltiazem, fendiline, gallopamil, mibefradil, prenylamine, semotiadil, terodiline, verapamil, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, perhexiline, and fluspirilene.

In one embodiment of the present invention, the CCB is amlodipine. Any of the optical isomer, enantiomer, diastereomer, racemate or racemic mixture, pharmaceutically acceptable salts, or pharmaceutically acceptable esters, of amlodipine can be used in the present invention.

In one embodiment, a racemic mixture of amlodipine or (R,S)-amlodipine, is used in the present invention.

In a preferred embodiment, a substantially optically pure (S)-(−)-amlodipine, such as a substantially optically pure (S)-(−)-amlodipine besylate, (S)-(−)-amlodipine mesylate or S)-(−)-amlodipine maleate, is used in the present invention.

According to embodiments of the present invention, dextromethorphan and the CCB can be administered together in the same pharmaceutical composition, or separately in different pharmaceutical compositions, so long as the dosing schedules of DM and the CCB overlap in time.

In an embodiment of the present invention, the CCB and DM are administered in a dosage ratio of CCB:DM as 1:0.5 to 1:100, e.g., 1:1, 1:5, 1:10, 1:20, 1:30, 1:40, 1:50, 1:60, 1:70, 1:80, 1:90 or 1:100, in the same pharmaceutical composition, e.g., a dosage form comprising both CCB and DM, or in separate pharmaceutical compositions, e.g., a separate dosage form for each of CCB and DM.

Another general aspect of the present invention relates to a pharmaceutical composition for treating hypertension or a symptom associated therewith in a subject, which comprises an effective amount of dextromethorphan, an effective amount of a calcium channel blocker, and a pharmaceutically acceptable carrier.

Embodiments of the present invention also relate to a pharmaceutical composition for treating hypertension or a symptom associated therewith in a subject, which comprises an effective amount of a calcium channel blocker, an effective amount of a NADPH oxidase inhibitor, and a pharmaceutically acceptable carrier.

Any of the CCBs effective for treating hypertension in a subject, such as those described above, can be used in the present invention.

Examples of NADPH oxidase inhibitor that can be used in the present application include, but are not limited to, gp91ds-tat, apocynin, diphenylene iodonium, aminoethyl benzenesulfono fluoride, S17834, PR39, protein kinase C inhibitors, VAS2870, angiotensinconverting enyzme inhibitors, angiotensin receptor blockers, statins, and dextromethorphan.

The pharmaceutical compositions according to embodiments of the present invention can optionally comprise other therapeutically active ingredients, such as another class of antihypertensive agent.

Embodiments of the present invention also relate to methods of treating hypertension or a symptom associated therewith in a subject. The methods comprising administering to the subject an effective amount of a NADPH oxidase inhibitor, such as dextromethorphan, and an effective amount of a CCB, such as amlodipine.

The NADPH oxidase inhibitor and the CCB can be administered together in a single pharmaceutical composition, separately at approximately the same time, or separately on separate dosing schedules. All that is required is that the dosing schedules of the NADPH oxidase inhibitor and the CCB overlap in time and thus are being followed concurrently.

The methods according to embodiments of the present invention can optionally comprise administering to the subject other therapeutically active ingredients, such as another class of antihypertensive agent.

Whether administered alone or in combination with an additional therapeutic agent, the therapeutic active ingredient can be administered by any known route of administration, including, orally, topically, parenterally (including subcutaneous, intravenous, intramuscular, and intrasternal injection or infusion administration techniques), by inhalation spray or rectally in dosage units or pharmaceutical compositions containing conventional pharmaceutically acceptable carriers and any such dosage units or pharmaceutical compositions are within the scope of the present invention.

Pharmaceutical compositions adapted for oral administration include solid forms such as pills, tablets, caplets, and hard or soft capsules (each including immediate release, timed release, and sustained release formulations) as well as lozenges and dispersible powders or granules. Liquid forms of pharmaceutical compositions adapted for oral administration include solutions, syrups, elixirs, emulsions, and aqueous or oily suspensions. Any of these dosage forms may be prepared according to any method or compounding technique known in the art for the manufacture of pharmaceutical compositions. Pharmaceutically acceptable carriers that may be desirably utilized in the manufacture of solid oral dosage forms include inert diluents, such as calcium carbonate, sodium carbonate, lactose, calcium phosphate or sodium phosphate; granulating or disintegrating agents, such as corn starch or alginic acid; binding agents, such as starch, gelatin, or acacia; and lubricating agents such as magnesium stearate, stearic acid or talc. If desired, solid pharmaceutical compositions adapted for oral administration may further include one or more sweetening agents, flavoring agents, coloring agents, or preserving agents in order to provide attractive or palatable preparations.

In those embodiments wherein the dosage form is a tablet or pill, it may either be uncoated or coated, and if coated, may be coated by any known technique. Further, the coating, if desirably provided, can be formulated or applied by known techniques so that the coating can delay disintegration of the tablet or pill, and thus, absorption of the active ingredient, thereby providing a controlled and/or sustained release dosage form capable of providing sustained therapeutic or prophylactic effect over a longer period. For example, the tablet or pill can comprise an inner dosage and an outer dosage component, the latter being in the form of an envelope over the former. An enteric layer that serves to resist disintegration in the stomach and permits the inner component to pass substantially intact into the duodenum or to be delayed in release can separate the two components. A variety of materials can be used for such enteric layers or coatings, including a number of polymeric acids, shellac, cetyl alcohol and cellulose acetate. Alternatively, in those embodiments wherein such a controlled and or sustained release is desired, tablets, pills or capsules may be formulated as osmotic pump dosage forms by any known method.

Pharmaceutical compositions adapted for oral administration may also be presented as hard or soft gelatin capsules, wherein the active ingredient may be mixed with an inert solid diluent, such as calcium carbonate, calcium phosphate or kaolin in the case of the former or with water or miscible solvents such as propylene glycol, PEG's and ethanol, or an oil medium such as peanut oil, liquid paraffin, or olive oil in the case of the latter.

Aqueous suspensions can be prepared that contain the active ingredient(s) in admixture with excipients suitable for the manufacture of aqueous suspensions. Such excipients include suspending agents, such as sodium carboxymethylcellulose, methylcellulose, hydroxypropylmethylcellulose, sodium alginate, polyvinyl-pyrrolidone, gum tragacanth and gum acacia, dextran, polyvinyl-pyrrolidone or gelatin; and dispersing or wetting agents such as lecithin, polyoxyethylene stearate, heptadecaethyleneoxycetanol, polyoxyethylene sorbitol monooleate, and polyethylene sorbitan monooleate. Aqueous suspensions may also contain one or more preservatives, such as ethyl or n-propyl, p-hydroxybenzoate; one or more coloring agents, one or more flavoring agents, and one or more sweetening agents, such as sucrose, saccharine or aspartame.

Oily suspensions may be formulated by suspending the active ingredient(s) in a vegetable oil, such as cottonseed, olive, sesame or coconut oil, or in a mineral oil, such as liquid paraffin. The oily suspensions may contain a thickening agent, such as beeswax, hard paraffin, or cetyl alcohol. Sweetening agents such as those set forth above, and flavoring agents may be added to provide a palatable oral preparation. Such oily suspensions may be preserved by the inclusion of an anti-oxidant such as ascorbic acid.

Dispersible powders and granules suitable for the preparation of an aqueous suspension suitable for oral administration can provide the active ingredient(s) in admixture with a dispersing or wetting agent, suspending agent, and one or more preservatives, all of which have been discussed above. Sweetening, flavoring, or coloring agents may also be present, if desired.

Pharmaceutical compositions suitable for oral administration may also be presented in the form of an oil-in-water emulsion. The oily phase may be a vegetable or mineral oil, such as those described above, or mixtures of these. Suitable emulsifying agents may be naturally-occurring phosphatides, such as soy bean, lecithin, sorbitan monooleate, or polyoxyethylene sorbitan monooleate. The emulsions may also contain sweetening or flavoring agents.

Syrups and elixirs may be formulated with sweetening agents, for example, glycerol, propylene glycol, sorbitol or sucrose. Such formulations may also contain a demulcent, a preservative and flavoring or coloring agents.

The pharmaceutical compositions may be further provided in a form adapted for parenteral administration, i.e., by injection or infusion. Injectable aqueous or oleaginous suspensions are desirably sterile and may be formulated according to known methods using suitable dispersing, wetting and suspending agents as mentioned above. A parenterally-acceptable diluent or solvent may also be utilized, such as 1,3-butanediol, water, Ringer's solution, and isotonic sodium chloride. Cosolvents such as ethanol, propylene glycol or polyethylene glycols may also be used. In addition, sterile, fixed oils are conventionally employed as solvents or suspending mediums in injectable or infusible solutions, and these may include any bland fixed oil, such as any of the synthetic mono- or diglycerides. Fatty acids such as oleic acid also may be utilized in the preparation of injectable or infusible solutions.

The pharmaceutical composition may also be presented in the form of a suppository. Suppositories can be formulated by mixing the active ingredient(s) and any additional desired therapeutic agent(s) with a suitable non-irritating excipient that is solid at room temperature but molten at body temperature, thereby releasing the active ingredient(s). Suitable materials include cocoa butter and polyethylene glycols.

For topical use, creams, ointments, gels, solutions or suspensions containing the active ingredient(s) may be prepared. As used herein, topical use includes mouth washes and gargles. Topical formulations may include cosolvents, emulsifiers, penetration enhancers, preservatives, emollients, and the like.

The active ingredients according to embodiments of the present invention can also be provided in a pharmaceutical composition in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

Preferably, pharmaceutical compositions according to embodiments of the present invention are formulated for oral administration. The pharmaceutical compositions may be conveniently presented in dosage form, and prepared by any of the methods known in the art of pharmacy in view of the present disclosure. In general, the pharmaceutical compositions are prepared by uniformly and intimately admixing the active ingredient with liquid carriers or finely divided solid carriers or both, and then, if necessary, shaping the product into the desired presentation.

The amount of therapeutically active ingredients to be included in a dosage form will depend upon the patient being treated, the mode of administration and the desired delivered dose. Representative pharmaceutical compositions will generally include from about 0.01 mg to about 1000 mg, from about 0.1 mg to 500 mg, from about 1 mg to about 100 mg, or from about 10 mg to about 100 mg, of the active ingredients.

In an embodiment of the present invention, each dosage form for oral administration, such as a pill, a tablet, a caplet, a hard or soft capsule, comprises about 10 mg to about 100 mg of an NADPH oxidase inhibitor, such as DM. Each of the dosage form can further comprise 10 mg to about 100 mg of a CYP2D6 inhibitor, such as quinidine. Each of the dosage form can additionally comprise about 0.5 mg to about 10 mg of a CCB, such as AM.

In another embodiment of the present invention, each dosage form for oral administration, such as a pill, a tablet, a caplet, a hard or soft capsule, comprises a ratio of a CCB (such as AM): a NADPH oxidase inhibitor (such as DM) of 1:0.5 to 1:100, e.g., 1:1, 1:5, 1:10, 1:20, 1:30, 1:40, 1:50, 1:60, 1:70, 1:80, 1:90 or 1:100.

In the case where an oral pharmaceutical composition is employed, a suitable dosage range of a NADPH, such as dextromethorphan, for use in the present invention is from about 0.1 mg to about 500 mg total daily dose, given as a once daily administration in the morning or in divided doses if required. Preferably, a dose range of between about 1 mg to about 300 mg is given as a once daily administration or in divided doses if required, and most preferably a dose range of from between about 10 mg to about 100 mg, or a dose range of from between about 20 mg to about 50 mg is given as a once daily administration or in divided doses if required. Patients may be upward titrated from below to within this dose range to a satisfactory control of symptoms or blood pressure as appropriate.

In the case where an oral pharmaceutical composition is employed, a suitable dosage range of a CCB, such as amlodipine, for use in the present invention is from about 0.01 mg to about 100.0 mg total daily dose, given as a once daily administration in the morning or in divided doses if required. Preferably, a dose range of between about 0.5 mg to about 20.0 mg is given as a once daily administration or in divided doses if required, and most preferably a dose range of from between about 0.5 mg to about 10.0 mg is given as a once daily administration or in divided doses if required. Patients may be upward titrated from below to within this dose range to a satisfactory control of symptoms or blood pressure as appropriate.

This invention will be better understood by reference to the non-limiting example that follows, but those skilled in the art will readily appreciate that the example is only illustrative of the invention as described more fully in the claims which follow thereafter.

Example 1

Animal Study on the Monotherapy and Combined Therapy of Dextromethorphan and Amlodipine An in vivo study was conducted to measure and compare the anti-hypertensive efficacy and tolerability of dextromethorphan and amlodipine in monotherapy and combined therapy in spontaneous hypertensive rats, an animal model for hypertension. The same study can be performed with other NADPH oxidase inhibitor and CCB.

Materials and Methods

Animals

The investigation conforms to the Guide for the Care and Use of Laboratory Animals published by the US National Institutes of Health (NIH Publications no. 85-23, revised 1996) and complies with the current Taipei Veterans General Hospital laws. Aged 18-week male normotensive Wistar Kyoto (WKY) and spontaneous hypertensive rats (SHR) were used in this study.

Untreated WKY and SHR were compared with SHR treated with amlodipine (1, 5 mg/kg/day) or dextromethorphan (1, 5, 25 mg/kg/day) and fix dose combination (AM+DM) using a matrix combination of above doses for 4 weeks. All the treatment groups are listed in Table 1, including G1~G12 for SHR and G0 for WKY as a control.

TABLE 1

| Treatment groups | | | |
|---|---|---|---|
| Treatment* | A0 | A1 | A2 |
| D0 | G1 | G5 | G9 |
| D1 | G2 | G6 | G10 |
| D2 | G3 | G7 | G11 |
| D3 | G4 | G8 | G12 |

*A0: no drug; A1: 1 mg/kg/day; and A2: 5 mg/kg/day of amlodipine treatment. D0: no drug; D1: 1 mg/kg/day; D2: 5 mg/kg/day; and D3: 25 mg/kg/day of dextromethorphan treatment.

Experimental Design

As aforementioned in Table 1, rats were divided into several experimental groups as follows:

G0: WKY as control (normotensive rats without drugs, n=10)
G1: SHR (hypertensive rats without drugs, n=10)
G2: SHR+D1 (DM 1 mg/kg/day, n=10)
G3: SHR+D2 (DM 5 mg/kg/day, n=10)
G4: SHR+D3 (DM 25 mg/kg/day, n=10)
G5: SHR+A1 (AM 1 mg/kg/day, n=10)
G6: SHR+A1+D1 (AM 1 mg/kg/day+DM 1 mg/kg/day, n=10)
G7: SHR+A1+D2 (AM 1 mg/kg/day+DM 5 mg/kg/day, n=10)
G8: SHR+A1+D3 (AM 1 mg/kg/day+DM 25 mg/kg/day, n=10)
G9: SHR+A2 (AM 5 mg/kg/day, n=10)
G10: SHR+A2+D1 (AM 5 mg/kg/day+DM 1 mg/kg/day, n=10)
G11: SHR+A2+D2 (AM 5 mg/kg/day+DM 5 mg/kg/day, n=10)
G12: SHR+A2+D3 (AM 1 mg/kg/day+DM 25 mg/kg/day, n=10)

Control rats (G0 and G1) received 1% solution of methylcellulose (1 ml/kg) by a gavage as a vehicle. AM and DM were suspended in 1% solution of methylcellulose and administered by a gavage in a 1 ml/kg volume. All compounds were administered for 4 weeks. Arterial blood pressure measurement and blood sampling were carried out before treatment, and after the second and forth week of drug administration.

Blood Pressure Determination

Arterial blood pressure was measured in conscious rats with an automatic sphygmomanometer, using tail-cuff method. Before the measurements, the animals were placed inside a warming chamber (about 34° C.) for 30 min. The aim of the procedure is to calm the animals and dilate the tail blood vessels. Arterial blood pressure was measured at least three times for each animal. Changes in pressure are expressed as the percentage of baseline values.

Biochemistry

Total cholesterol, LDL-cholesterol, ALT, AST and Creatinine are measured by using automatic biochemical analyzers (Spotchem™ SP 4410 Kyoto Daiichi Kagaku Co. Ltd.).

Serum Oxidative Stress and Inflammatory Markers

The oxidant systems include enzymes such as superoxide dismutase, catalase, and glutathionine peroxidase, macromolecules such as albumin, ceruloplasmin and ferritin, small molecules such as ascorbic acid, α-tocopherol, β-carotene, reduced gluthionine, uric acid and bilirubin. The sum of the endogenous and food-derived antioxidants represents the total antioxidant activity of the system. The total antioxidant capacity or total antioxidant status (TAS, mmol/L) of plasma, serum, urine, saliva, or cell lysates, can be measured using commercially available kits, such as Antioxidant Assay Kit (Cat No. 709001, Cayman) or Total Antioxidant Status, Randox Lab Ltd), with results expressed as mmol/L, following the kit's protocol.

In addition, serum peroxynitrate (3-nitrotyrosine, 3-NT), 8-Hydroxydeoxyguanosine(8-OHdG), endothelin-1 (ET-1), superoxide dismutase (SOD) and glutathione peroxidase (GPx) activities (IU/g Hb) are also assessed.

Nitrotyrosine is formed in presence of the active metabolite NO. Various pathways including the formation of peroxinitrite lead to nitrotyrosine production. Since nitrotyrosine is a stable end product of peroxynitrite oxidation, assessment of its plasma concentration may be useful as a marker of NO-dependent damage in vivo. The presence of nitrotyrosine has been detected in various inflammatory processes including atherosclerotic plaques, celiac disease, rheumatoid arthritis, chronic renal failure and septic shock. Nitrotyrosine has also been identified as a marker of inflammation. In normal plasma low, undetectable, levels of nitrotyrosine are present. Quantitative determination of nitrotyrosine in plasma and other biological samples can be performed using commercially available kits, such as Nitrotyrosine ELISA kit (Hycult Biotech, HK501)

8-OHdG is produced by oxidative damage of DNA by reactive oxygen and nitrogen species and serve as an established marker of oxidative stress. Increased 8-OH-dG are associated with hypertension, as well as aging process and a number of other conditions, such as cancer and diabetes. Quantitative determination of 8-OHdG in plasma and other biological samples can be performed using commercially available kits, such as 8-hydroxy-2-deoxy Guanosine EIA Kit (Cayman, Cat No. 589320 or 589321)

Endothelin-1 (ET-1), a peptide of 21 amino acid residues, is the most potent vasoconstrictor substance known. ET-1 has been shown to have potent effects on smooth muscle cells, fibroblasts and to be involved in many disease processes, particularly cardiovascular diseases. It has been shown to be important in congestive heart failure, renal failure and pulmonary hypertension. Quantitative determination of 8-OHdG in plasma and other biological samples can be performed using commercially available kits, such as Endothelin-1 Assay Kit (L) (IBL, Code No. 27165).

The 3-NT, 8-OhdG, ET-1 can also be measured in duplicate with commercially available enzyme-linked immunosorbent assay kits (Quantikine, R&D Systems, USA) according to the manufacturer's instructions.

These assays are based on a two-site ELISA sandwich format using two antibodies directed against different epitopes of MMPs. The 96-well microplate is precoated with antibody to MMPs. The plasma samples are added into the microplate and the detection of antibody conjugated to horseradish peroxidase is added. Then tetramethylbenzidine (TMB) substrate is used. The reaction of peroxide-TMB is stopped by the addition of sulfuric acid and the resultant color measured at 450 nm in a microplate spectrophotometer. Thus, 100-μL samples are analysed in duplicate with working standards and measured on a microplate reader (Asys-Hitech, Austria). After a standard curve is constructed, sample values are determined using microplate reader with software (version 3.1, Asys-Hitech, Austria).

SOD and GPx activities, expressed as IU/g Hb, are assessed using commercially available kits (Ransod and Ransel, respectively, from Randox Lab Ltd, Crumlin, UK).

Products of lipid peroxidation, namely, malondialdehyde (MDA), are evaluated by the thiobarbituric acid (TBA) assay. The assay mixture consisted of 0.1 mL serum, 0.4 mL 0.9% NaCl, 0.5 mL 3% sodium dodecylsulfate (SDS), and 3 mL TBA reagent (containing equal parts of 0.8% aqueous TBA and acetic acid); the mixture is heated for 75 minutes at 95° C. and, thereafter, 1 mL cold 0.9% NaCl and extracted with 5 mL n-butanol. After centrifugation at 730 g for 15 minutes at 4° C., the organic phase is analyzed spectrophotometrically at 532 nm, using 1,1,3,3-tetramethoxypropane as an external standard. The results are expressed as μmol/L of MDA.

Measurement Time Points

Figure 6:
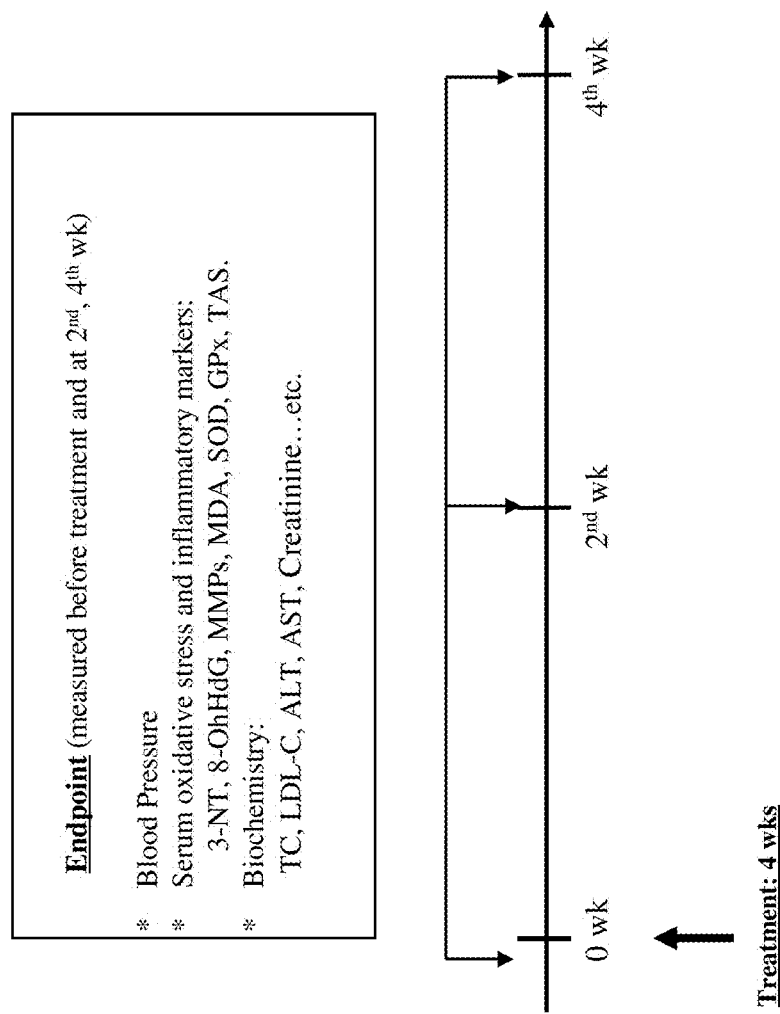
FIG. 6 is a flow chart showing the different time points when blood pressure were measured and blood sampling were taken in the animal study.

Arterial blood pressure and blood sampling will be measured before treatment, and after the second and forth week of drug administration (FIG. 6).

Statistical Analysis

Results are expressed as mean±SD. The normality of distribution was checked by means of Kolmogorov-Smirnov test with Lilliefors test. The statistical evaluation was performed using analysis of variance (ANOVA) and post hoc comparisons were performed by means of Least Significant Differences (LSD) test. If the data were not normally distributed, statistical evaluation was performed by using ANOVA (Kruskall-Wallis) and Mann-Whitney U test. Differences were considered significant when $p<0.05$.

Table 2 lists the blood pressure measurements of the control groups, i.e., WKY and SHR, measured before and after the rats were given with the blank treatment (1% solution of methylcellulose). As shown in Table 2, the blood pressure measurements generally stayed the same at the two measure points.

TABLE 2

Blood pressure measurements of the control groups

|  | WKY | SHR |
| --- | --- | --- |
| SBP(Before) | 126.42 | 202.82 |
| SBP(After) | 124.16 | 209 76 |
| DBP(Before) | 91.64 | 165.48 |
| DBP(After) | 94.00 | 178.90 |
| HR(Before) | 292.08 | 401.80 |
| HR(After) | 335.04 | 418.28 |
| MBP(Before) | 103.00 | 178.20 |
| MBP(After) | 103.96 | 189.04 |

As shown in FIGS. 1a-d, treatment with DM alone at three different dosage levels, 1 mg/kg/day, 5 mg/kg/day, and 25 mg/kg/day, all resulted in lowering of the blood pressure in SHR. However, no clear dosage response was observed.

As shown in FIGS. 2a-d, treatment with AM alone at two different dosage levels, 1 mg/kg/day and 5 mg/kg/day, also resulted in lowering of the blood pressure in SHR. The blood pressure lowering effect is more pronounced with the higher dose AM treatment.

As shown in FIGS. 3a-d, combined treatment with DM and AM at various dosage levels dramatically improved the blood pressure lowing effects of each of DM and AM.

As more clearly illustrated in FIGS. 4a-4d and FIGS. 5a and 5b, the blood pressure lowering effect of DM and AM, particularly as measured by systolic blood pressure (SBP), is greater than the additive effect of DM and AM alone separately. This indicates that DM and AM act synergistically in lowering the blood pressure.

Example 2

Endothelium-Dependent Vasorelaxation Study

The mechanism of the blood pressure lowering effect of dextromethorphan or its synergistic action with a calcium channel blocker in the treatment of hypertension is studied by an endothelium-dependent vasorelaxation study, which measures isometric tension of rat aortic ring in response to drugs. In particular, the effect of the testing drug, e.g., dextromethorphan, amlodipine, or a combination of dextromethorphan and amlodipine on high KCl-induced contractions are studied, e.g., by measuring the cumulative concentration-response curves to the endothelium-dependent and endothelium-independent relaxant agonists acetylcholine (ACh) and sodium nitroprusside (SNP), respectively, or to the 1-receptor agonist phenylephrine (PE).

Aortic Ring Preparation

The rats are anaesthetized with pentobarbital (60 mg kg-1 of body weight, i.p.), descending thoracic aorta is dissected, cut into small rings (3-5 mm in width) and suspended in a 5 ml organ bath containing normal Krebs physiological salt solution (KPSS) of the following compositions (mM): NaCl 118.2, KCl 4.7, $CaCl_2 \cdot 2H_2O$ 2.5, $KH_2PO_4$ 1.2, $MgCl_2$ 1.2, glucose 11.7, $NaHCO_3$ 25.0, and EDTA 0.026. The bathing solution is gassed continuously with 95% oxygen and 5% carbon dioxide at 37° C. (pH 7.4).

Isometric tension (g) is measured using a force displacement transducer connected to a Mac Lab recording system (ADI Instruments, Australia). Aortic rings are then progressively stretched to an optimal basal tension of 1 g and allowed to equilibrate for 45 min. During this period, the bathing solution is replaced every 15 min and, if needed, the basal tone is readjusted to 1 g.

Aortic rings are then repeatedly stimulated with KCl solution (high $K^+$, 80 mM) for 5 min at 10 min intervals until two consecutive equal contractions are attained—evidence of tissue stability.

Pharmacological Studies

Following washout of high $K^+$ responses, the aortic rings are incubated for 20 min with the testing drug, e.g., dextromethorphan, amlodipine, or a combination of dextromethorphan and amlodipine or its vehicle (control), and cumulative concentration-response curves to the endothelium-dependent and endothelium-independent relaxant agonists acetylcholine (ACh, $10^{-10}$ to $10^{-5}$M) and sodium nitroprusside (SNP, $10^{-11}$ to $10^{-6}$ M), respectively, or to the 1-receptor agonist phenylephrine (PE, $10^{-10}$ to $10^{-5}$ M) are then measured. To test the relaxation responses to ACh and SNP, the aortic rings are pre-contracted with PE (1 µM).

The concentrations of the testing drug are chosen based on the physiologically achievable plasma concentrations of the drug. In experiments to characterize the mechanisms involved in the effects of the testing drugs, the aortic rings are exposed to various pharmacological agents for 5 min before the incubation with the drug or its vehicle.

Where indicated, endothelium is removed by gently rubbing the intimal surface of the vessel with the blunted forceps. The endothelium is considered effectively removed if ACh (1 µM) caused less than 10% relaxation of aortic rings pre-contracted with PE.

To examine the possible role of nitric oxide, prostacyclin, and the cyclic GMP relaxant pathway in the effects of the testing drug, the concentration-response curves to ACh are measured in aortic rings incubated with and in continued presence of N-nitro-1-arginine methyl ester (L-NAME, 10 µM)—an eNOs inhibitor, indomethacin (10 µM)—a cyclooxygenase inhibitor, and methylene blue (10 µM)—a cyclic GMP inhibitor, respectively.

To examine the contribution of endothelium-derived hyperpolarizing factor (EDHF) or potassium (K+) channels in the effects of the test drug, the aortic rings are partially depolarized by increasing concentration of KCl in the KPSS (4.8-20 mM), and the concentration-response curves to ACh is then performed.

Statistical Analysis

The contractile responses of aortic rings to graded concentrations of PE are expressed as percentages of the maximum contractile effect of high $K^+$ in respective tissues.

The vasodilator effect of increasing concentrations of ACh or SNP are expressed as percent decrease of the peak PE ($10^{-6}$ M) contraction.

The concentration-response curve for each experimental condition is plotted and from it are deduced the values of maximal contraction (Cmax) or maximal relaxation (Rmax) and the concentration of the testing drug (expressed as negative log molar) producing 50% of maximum contraction or relaxation (pEC50) recorded (Prism Version 2.0, GraphPad Software, USA).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCE

1. Kearney P M, Whelton M, Reynolds K, et al. Global burden of hypertension: Analysis of worldwide data. *Lancet*. 2005; 365:217-223.
2. Ong K L, Cheung B M, Man Y B, et al. Prevalence, awareness, treatment, and control of hypertension among United States adults 1999-2004. *Hypertension*. 2007; 49:69-75.
3. Ezzati M, Lopez A D, Rodgers A, et al, for the Comparative Risk Assessment Collaborating Group. Selected major risk factors and global and regional burden of disease. *Lancet*. 2002; 360:1347-1360.
4. O'Connor P J. Improving medication adherence: Challenges for physicians, payers, and policy makers. Arch Intern Med. 2006; 166:1802-1804.
5. Nelson M R, Reid C M, Ryan P, et al. Self-reported adherence with medication and cardiovascular disease outcomes in the Second Australian National Blood Pressure Study (ANBP2). Med J Aust. 2006; 185:487-489.
6. Mounier-Vehier C, Bernaud C, Cart6 A, et al. Compliance and antihypertensive efficacy of amlodipine compared with nifedipine slow-release. Am J Hypertens. 1998; 11:478-486.
7. Chobanian A V, Bakris G L, Black H R, et al, for the Joint National Committee on Prevention, Detection, Evaluation, and Treatment of High Blood Pressure; the National Heart, Lung, and Blood Institute; and the National High Blood Pressure Education Program Coordinating Committee. Seventh report of the Joint National Committee on Prevention, Detection, Evaluation, and Treatment of High Blood Pressure. Hypertension 2003; 42:1206-1252.
8. Mancia G, De Backer G, Dominiczak A, et al, for the Task Force for the Management of Arterial Hypertension of the European Society of Hypertension and the European Society of Cardiology. 2007 Guidelines for the management of arterial hypertension: The Task Force for the Management of Arterial Hypertension of the European Society of Hypertension (ESH) and of the European Society of Cardiology (ESC). Eur Heart J. 2007; 28:1462-1536.
9. Staessen J A, Fagard R, Thijs L, et al, for the Systolic Hypertension in Europe (Syst-Eur) Trial Investigators. Randomised double-blind comparison of placebo and active treatment for older patients with isolated systolic hypertension. Lancet. 1997; 350:757-764.
10. Liu L, Wang J G, Gong L, et al, for the Systolic Hypertension in China (Syst-China) Collaborative Group. Comparison of active treatment and placebo in older Chinese patients with isolated systolic hypertension. J Hypergens. 1998; 16:1823-1829.
11. Brown M J, Palmer C R, Castaigne A, et al. Morbidity and mortality in patients randomised to doubleblind treatment with a long-acting calcium-channel blocker or diuretic in the International Nifedipine GITS study: Intervention as a Goal in Hypertension Treatment (INSIGHT) [published correction appears in Lancet. 2000; 356:514]. Lancet. 2000; 356:366-372.

12. Hansson L, Zanchetti A, Carruthers S G, et al, for the HOTStudy Group. Effects of intensive blood-pressure lowering and low-dose aspirin in patients with hypertension: Principal results of the Hypertension Optimal Treatment (HOT) randomized trial. Lancet. 1998; 351:1755-1762.
13. The ALLAHAT Officers and Coordinators for the ALLHAT Collaborative Research Group. Major outcomes in high-risk hypertensive patients randomized to angiotensinconverting enzyme inhibitor or calcium channel blocker vs diuretic: The Antihypertensive and Lipid-Lowering Treatment to Prevent Heart Attack Trial (ALLHAT). JAMA. 2002; 288:2981-2997.
14. Dahlof B, Sever P S, Poulter N R, et al, for the ASCOT Investigators. Prevention of cardiovascular events with an antihypertensive regimen of amlodipine adding perindopril as required versus atenolol adding bendroflumethiazide as required, in the Anglo-Scandinavian Cardiac Outcomes Trial-Blood Pressure Lowering Arm (ASCOT-BPLA): A multicentre randomised controlled trial. Lancet. 2005; 366:895-906.
15. Packer M, O'Connor C M, Ghali J K, et al, for the Prospective Randomized Amlodipine Survival Evaluation Study Group. Effect of amlodipine on morbidity and mortality in severe chronic heart failure. N Engl J Med 1996; 335:1107-1114.
16. Julius S, Kjeldsen S E, Weber M, et al, for the VALUE Trial Group. Outcomes in hypertensive patients at high cardiovascular risk treated with regimens based on valsartan or amlodipine: The VALUE randomized trial. Lancet. 2004; 363:2022-2031.
17. Tortella F C, Pellicano M, and Bowery N G (1989) Dextromethorphan and neuromodulation: old drug coughs up new activities. Trends Pharmacol Sci 10:501-507.
18. George C P, Goldberg M P, Choi D W, and Steinberg G K (1988) Dextromethorphan reduces neocortical ischemic neuronal damage in vivo. Brain Res 440:375-379.
19. Monyer H and Choi D W (1988) Morphinans attenuate cortical neuronal injury induced by glucose deprivation in vitro. Brain Res 446:144-148.
20. Prince D A and Feeser H R (1988) Dextromethorphan protects against cerebral infarction in a rat model of hypoxia-ischemia. Neurosci Lett 85:291-296.
21. Steinberg G K, George C P, DeLaPaz R, Shibata D K, and Gross T (1988) Dextromethorphan protects against cerebral injury following transient focal ischemia in rabbits. Stroke 19:1112-1118.
22. Britton P, Lu X C, Laskosky M S, and Tortella F C (1997) Dextromethorphan protects against cerebral injury following transient, but not permanent, focal ischemia in rats. Life Sci 60:1729-1740.
23. Tortella F C, Britton P, Williams A, Lu X C, and Newman A H (1999) Neuroprotection (focal ischemia) and neurotoxicity (electroencephalographic) studies in rats with AHN649, a 3-amino analog of dextromethorphan and low-affinity N-methyl-Daspartate antagonist. J Pharmacol Exp Ther 291:399-408.
24. Wei Zhang, Tongguang Wang, Liya Qin, Hui-Ming Gao, Belinda Wilson, Syed F. Ali, Wanqin Zhang, Jau-Shyong Hong, And Bin Liu (2004). Neuroprotective effect of dextromethorphan in the MPTP Parkinson's disease model: role of NADPH oxidase1. FASEB 18:589-591.
25. Y Alvarez, A M Briones, R Hernanz, J V Pe'rez-Giro'n, M J Alonso and M Salaices (2008). Role of NADPH oxidase and iNOS in vasoconstrictor responses of vessels from hypertensive and normotensive rats. British Journal of Pharmacology 153, 926-935.

The invention claimed is:

1. A method of treating hypertension in a subject, comprising administering to a subject suffering from hypertension an effective amount of dextromethorphan and an effective amount of amlodipine, whereby the blood pressure of the patient is lowered.

2. The method of claim 1, wherein the dextromethorphan and the amlodipine are administered in a pharmaceutical composition comprising dextromethorphan, amlodipine, and a pharmaceutically acceptable carrier.

3. The method of claim 1, further comprising administering to the subject a CYP2D6 inhibitor that is effective to prolong the half-life of dextromethorphan in the subject.

4. The method of claim 3, wherein the CYP2D6 inhibitor is quinidine.

5. The method of claim 1, wherein the amlodipine is a substantially optically pure S-(−)-amlodipine.

* * * * *